US012660998B2

(12) United States Patent
Chin et al.

(10) Patent No.: US 12,660,998 B2
(45) Date of Patent: *Jun. 23, 2026

(54) OSCILLATING ENDOSCOPIC CATHETER FOR FALLOPIAN TUBE NAVIGATION

(71) Applicant: FemDX Medsystems, Inc., Palo Alto, CA (US)

(72) Inventors: Albert K. Chin, Palo Alto, CA (US); Pei-Jie Cao, Newark, CA (US)

(73) Assignee: FemDx Medsystems, Inc., Santa Clara, CA (US)

( * ) Notice: Subject to any disclaimer, the term of this patent is extended or adjusted under 35 U.S.C. 154(b) by 823 days.

This patent is subject to a terminal disclaimer.

(21) Appl. No.: 18/020,621

(22) PCT Filed: May 25, 2021

(86) PCT No.: PCT/US2021/034100
§ 371 (c)(1),
(2) Date: Feb. 9, 2023

(87) PCT Pub. No.: WO2021/242779
PCT Pub. Date: Dec. 2, 2021

(65) Prior Publication Data
US 2023/0309812 A1 Oct. 5, 2023

Related U.S. Application Data

(63) Continuation of application No. 16/882,971, filed on May 26, 2020, now Pat. No. 11,602,269.
(Continued)

(51) Int. Cl.
*A61B 1/303* (2006.01)
*A61B 1/00* (2006.01)
(Continued)

(52) U.S. Cl.
CPC .......... *A61B 1/303* (2013.01); *A61B 1/00066* (2013.01); *A61B 1/00082* (2013.01);
(Continued)

(58) Field of Classification Search
CPC ...... A61M 25/0147; A61M 2025/0175; A61B 17/320002; A61B 2017/320028;
(Continued)

(56) References Cited

U.S. PATENT DOCUMENTS 4,462,408 A 7/1984 Silverstein et al.
5,596,989 A 1/1997 Morita
(Continued)

FOREIGN PATENT DOCUMENTS

CN 110753521 A 2/2020
JP S5673804 U 6/1981
(Continued)

OTHER PUBLICATIONS

Acquire: Endoscopic Ultrasound Fine Needle Biopsy Device. Boston Scientific. Mar. 2017. Retrieved Jun. 21, 2024 at URL: https://www.bostonscientific.com/content/dam/bostonscientific/endo/portfolio-group/Acquire-Biospy-FNB-Needle/acquire-product-brochure.pdf. pp. 1-4.
(Continued)

*Primary Examiner* — Nathan R Price
(74) *Attorney, Agent, or Firm* — Womble Bond Dickinson (US) LLP

(57) ABSTRACT
A falloposcope intended for use with a hysteroscope to access, image, and collect samples from a patient's fallopian tube includes a cannula having an angled tip oriented to engage a fallopian tube os when the cannula is transcervically introduced to a patient's uterus through the hysteroscope. The catheter has a distal viewing tip configured to be advanced from a distal end of the cannula into the patient's
(Continued)

uterus through a cervical os. A viewing chamber has a wide proximal end attached to the distal viewing tip of the catheter, and the viewing chamber is at least partially transparent and typically tapers in a distal direction to provide a clear viewing zone for the endoscope as well as atraumatic advancement into the fallopian tube.

14 Claims, 19 Drawing Sheets

Related U.S. Application Data

(60) Provisional application No. 63/115,776, filed on Nov. 19, 2020, provisional application No. 63/105,801, filed on Oct. 26, 2020.

(51) Int. Cl.

| | |
|---|---|
| *A61B 1/01* | (2006.01) |
| *A61B 10/04* | (2006.01) |
| *A61B 17/22* | (2006.01) |
| *A61M 25/00* | (2006.01) |
| *A61M 25/01* | (2006.01) |
| *A61B 17/00* | (2006.01) |
| *A61B 17/42* | (2006.01) |
| *A61B 90/00* | (2016.01) |

(52) U.S. Cl.
CPC ...... *A61B 1/00096* (2013.01); *A61B 1/00135* (2013.01); *A61B 1/00148* (2022.02); *A61B 1/00154* (2013.01); *A61B 1/0016* (2013.01); *A61B 1/01* (2013.01); *A61B 10/04* (2013.01); *A61B 17/22* (2013.01); *A61M 25/0068* (2013.01); *A61M 25/0082* (2013.01); *A61M 25/0133* (2013.01); *A61B 2017/00398* (2013.01); *A61B 2017/00407* (2013.01); *A61B 2017/00902* (2013.01); *A61B 2017/4233* (2013.01); *A61B 90/03* (2016.02); *A61M 2205/583* (2013.01); *A61M 2210/1425* (2013.01)

(58) Field of Classification Search
CPC ............ A61B 1/00066; A61B 1/00096; A61B 1/00135; A61B 1/00148; A61B 1/01; A61B 1/303
See application file for complete search history.

(56) References Cited

U.S. PATENT DOCUMENTS

| | | | | |
|---|---|---|---|---|
| 5,807,239 | A | * | 9/1998 | DiBernardo ............. A61B 1/07 |
| | | | | 600/114 |
| 5,935,098 | A | | 8/1999 | Blaisdell et al. |
| 7,678,106 | B2 | | 3/2010 | Lee |
| 9,028,401 | B1 | * | 5/2015 | Bacich ................... A61B 1/303 |
| | | | | 600/204 |
| 10,285,731 | B2 | * | 5/2019 | Adams ........... A61B 17/320016 |
| 10,335,233 | B2 | | 7/2019 | Sabado et al. |
| 11,602,269 | B2 | | 3/2023 | Chin et al. |
| 12,318,252 | B2 | | 6/2025 | Cao et al. |
| 2004/0030268 | A1 | | 2/2004 | Weng et al. |
| 2004/0220478 | A1 | | 11/2004 | Wallace et al. |
| 2011/0098530 | A1 | | 4/2011 | Yamane |
| 2013/0096600 | A1 | * | 4/2013 | Wesley ........... A61B 17/320016 |
| | | | | 606/187 |
| 2015/0351729 | A1 | | 12/2015 | Chin et al. |
| 2016/0287232 | A1 | | 10/2016 | Chao et al. |
| 2017/0245878 | A1 | | 8/2017 | Aljuri et al. |
| 2017/0258392 | A1 | | 9/2017 | Skieller et al. |
| 2019/0038300 | A1 | * | 2/2019 | Savastano ............. A61M 25/09 |
| 2019/0133696 | A1 | | 5/2019 | Spero |
| 2021/0059749 | A1 | | 3/2021 | Sharma et al. |
| 2021/0169312 | A1 | | 6/2021 | Morimoto et al. |
| 2021/0187261 | A1 | | 6/2021 | Murdeshwar et al. |
| 2022/0031377 | A1 | | 2/2022 | Ransbury et al. |
| 2023/0200780 | A1 | | 6/2023 | Cao et al. |
| 2023/0309812 | A1 | | 10/2023 | Chin et al. |

FOREIGN PATENT DOCUMENTS

| | | |
|---|---|---|
| JP | H0397431 A | 4/1991 |
| JP | 2014507986 A | 4/2014 |
| JP | 2014519925 A | 8/2014 |
| JP | 2014217552 A | 11/2014 |
| JP | 2018517452 A | 7/2018 |
| JP | 2019511266 A | 4/2019 |
| WO | WO-2013137372 A1 | 9/2013 |
| WO | WO-2014057813 A1 | 4/2014 |
| WO | WO-2017205646 A1 | 11/2017 |
| WO | WO-2019049159 A1 | 3/2019 |
| WO | WO-2019191705 A1 | 10/2019 |
| WO | WO-2021043572 A1 | 3/2021 |
| WO | WO-2021242779 | 12/2021 |

OTHER PUBLICATIONS

EP2021813009.4 Partial European Search Report dated May 21, 2024.

Fuccio, et al. Forward-viewing linear echoendoscope: a new option in the endoscopic ultrasound armamentarium (with video). Journal of Hepato-Biliary-Pancreatic Sciences 22(1):27-34 (2015). Published online Oct. 23, 2014.

U.S. Appl. No. 17/942,603 Office Action dated Apr. 17, 2024.

EP21813009.4 Extended European Search Report dated Aug. 12, 2024.

U.S. Appl. No. 17/942,603 Office Action dated Sep. 5, 2024.

PCT/US2021/034100 International Search Report and Written Opinion of the International Searching Authority dated Oct. 28, 2021.

U.S. Appl. No. 16/882,971 Notice of Allowance dated Feb. 1, 2023.

U.S. Appl. No. 16/882,971 Office Action dated Dec. 7, 2022.

Co-pending U.S. Appl. No. 19/201,524, inventors Cao; Pei-Jie et al., filed on May 7, 2025.

U.S. Appl. No. 17/942,603 Corrected Notice of Allowability dated May 5, 2025.

U.S. Appl. No. 17/942,603 Notice of Allowance dated Feb. 12, 2025.

* cited by examiner

38

63

62

64

40

OSCILLATING ENDOSCOPIC CATHETER FOR FALLOPIAN TUBE NAVIGATION

CROSS-REFERENCE TO RELATED APPLICATIONS

The application is a continuation-in-part and claims the benefit of U.S. application Ser. No. 16/882,971, filed May 26, 2020; this application also claims the benefit of 63/105, 801, filed Oct. 26, 2020, and U.S. Provisional No. 63/115, 776, filed Nov. 19, 2020, the content of each of which is fully incorporated herein by reference.

FIELD OF THE INVENTION

The present invention relates generally to devices and methods for endoscopic intrauterine fallopian tube access and navigation. More specifically, it relates to an oscillating transparent tapered-tipped endoscopic device employing force limitation that may be advanced to navigate the length of the fallopian tube.

BACKGROUND OF THE INVENTION

An endoscopic guided catheter is desired that may navigate through the fallopian tube without incurring trauma or perforation, for purposes of tubal recanalization for infertility, or for tubal cell sampling in the diagnosis of ovarian cancer. The fallopian tube is delicate and tortuous, and conventional methods of cannulation using guidewire and tapered catheter advancement may cause injury or perforation. Catheter advancement through the length of the fallopian tube is presently performed under fluoroscopic guidance, generally following contrast dye injection via a hysterosalpingogram (HSG). If the HSG demonstrates tubal occlusion, guidewire and catheter passage may be performed to attempt to recanalize the occlusion. The occurrence of tubal perforation during catheter recanalization of the fallopian tube has been previously estimated at 4% of procedures.

A linear everting balloon has also been used to deliver an endoscope called a falloposcope into the fallopian tube. The balloon is initially inverted into the lumen of the outer catheter, and the falloposcope resides inside the inverted balloon and inner catheter. The outer catheter is pressurized to 10 atm of pressure, and advancement of the inner catheter everts the balloon and the falloposcope forward in the fallopian tube. The falloposcope moves forward at twice the rate of the everting balloon, necessitating incremental falloposcope retraction during balloon eversion, to prevent the falloposcope tip from perforating the fallopian tube. In a published study on the use of linear everting balloon falloposcopy in 304 patients, tubal perforation was reported in 1.3% of patients.

Cannulation of the fallopian tube has also been performed using a linear everting balloon catheter inserted through the working channel of a 5.5 Fr rigid hysteroscope. The hysteroscope is advanced into the uterus and manipulated to visualize the os of the fallopian tube and to guide insertion of the linear everting balloon catheter into the tube. Introduction of a rigid hysteroscope into the uterus requires manipulation of the cervix with sharp pointed tenaculum forceps, causing severe pain to the patient. This painful procedure is generally difficult or impossible to perform as an in-office procedure. It is desirable to develop a technique and device that may allow fallopian tube passage to be performed in the physician's office on an annual screening basis, without the requirement for anesthesia to control pain during the procedure. Annual cell sampling from the fallopian tube is desired for screening to detect the occurrence of ovarian cancer, which has been demonstrated to derive from the fallopian tube. Ovarian cancer occurs with a ten-fold greater incidence in patients who carry the BRCA gene mutation. In the United States, there are 313,000 women between the ages of 15 to 80 who carry the BRCA gene mutation and require annual screening for the development of ovarian cancer. In addition, 250,000 women a year are diagnosed with an ovarian cyst, and at present, there is no non-surgical modality for determining whether an ovarian mass is a benign cyst or a malignant tumor. An atraumatic in-office device for fallopian tube cell sampling is desired, akin to the traditional Papinicoloau test, or Pap smear, for cervical cancer. In a Pap smear, a vaginal speculum is inserted to allow the introduction of a cotton-tipped applicator to the surface of the cervix for cytological cell collection. Use of a tenaculum forceps is unnecessary, and the procedure is performed as a standard annual in-office examination.

Previously, as described in commonly owned U.S. patent application Ser. No. 16/882,971, filed on May 26, 2020, a substantially rigid 5 mm diameter cannula with a slight bend in its distal portion possessed an inner lumen that contained a flexible balloon-tipped catheter and a CMOS-chip endoscope that resided within the transparent tapered balloon. The endoscopic balloon catheter was advanced through the fallopian tube in a reciprocally rotational manner, powered by a ratcheting mechanism and a rotational mechanism contained in the handle of the device. In addition, a force-limiting mechanism was incorporated into the ratchet advancement function, to guard against excessive tip advancement force that may lead to perforation of the fallopian tube. Due to the mechanically driven nature of balloon-tipped endoscopic catheter advancement, tactile feedback of catheter tip force exerted on fallopian tube tissue was limited in this design. A discrete amount of applied tip force was preset by the force-limitation mechanism.

It would be clinically desirable to provide a substantially instantaneous tactile feedback of the endoscopic catheter tip force to the operating physician. A variable amount of force may be required to traverse different segments of the fallopian tube, and the physician must be able to adjust the catheter advancement rate, rotational angle, rotational speed, and applied force depending upon the morphology of the individual tube. Therefore, a manually oscillating advancing endoscopic catheter is envisioned to allow the physician to perform visually guided cannulation of the full length of the fallopian tube.

SUMMARY OF THE INVENTION

The present invention comprises a substantially rigid cannula, typically having a slight angulation in its distal portion configured to be inserted into a patient's uterus and rotated to align the angled tip with the os of the fallopian tube. A transparent tapered-tipped catheter having a viewing element, such as a CMOS-chip endoscope, is configured to be distally advanced through an inner lumen of the cannula with the viewing element at a shoulder of the transparent tapered tip. A cell or tissue sampling element may be positioned immediately proximal to the transparent tapered tip, such as a gauze cuff disposed coaxially over an external surface of the catheter.

In an exemplary embodiment of the present invention, the gauze cuff may used to collect cells from an inner surface of the fallopian tube. A shoulder of the gauze cuff initially lies flush with the distal end of the cannula as the cannula is advanced under endoscopic guidance through the patient's cervical os and into the uterus. Most of the length of the transparent tapered tip lies distal to the distal end of the CMOS-chip endoscope, e.g. to provide a 5-7 mm long field of view ahead of the endoscope. Rotation of the cannula is performed to align the tapered-tipped endoscope with either the left or the right os of the fallopian tube. The endoscopic tapered-tipped catheter may be advanced into the fallopian tube while the distal end of the cannula remains outside the os of the fallopian tube. The tapered-tipped catheter is typically configured to rotationally oscillate (provided with a reciprocal rotational capability), rotating alternately clockwise and counter-clockwise in an arc of 20° to 120°, typically 60°, in either direction from an initial vertical position, while the cannula and the CMOS-chip endoscope inside the catheter remain stationary. The tapered-tipped catheter is advanced forward through a length of the fallopian tube lumen while reciprocal rotation is conducted. The reciprocal rotation allows the tapered-tipped catheter to be advanced through a delicate tubal structure that is characteristically tortuous, collapsed, and may be stenotic or occluded. The transparent tapered tip gently dissects through collapsed or occluded tubal segments with its reciprocal rotational movements, avoiding the perforation experienced with advancement of a guidewire and 3 Fr catheter in a similar setting. A reciprocal rotation of the catheter is used instead of a unidirectional rotation, to avoid twisting and winding of the tube in the event of friction and adhesion of the tapered-tipped catheter to the inner surface of the fallopian tube. Due to the delicate nature of the fallopian tube, traction and twisting may result in tubal perforation or transection.

The cannula may be constructed of a polymeric material such as polyurethane, nylon, or polyethylene, or it may be constructed of stainless steel with an outer coating of polymer to provide atraumatic passage through the cervix into the uterus The outer diameter of the cannula is typically 3-5 mm, usually being approximately 4 mm, with a working length of 20-30 cm, usually approximately 25 cm, and the distal 1 cm of its tip may incorporate approximately a 20° bend angle. The transparent tapered conical tip may have a maximal outer diameter of approximately 1-1.3 mm, a rounded distal tip of 0.2-0.3 mm radius, and a length of approximately 7-10 mm.

The transparent tapered tip may be rigid, semi-rigid, flexible, or elastic, or combinations thereof. In certain instances, the transparent tapered tip will have a rigid or semi-rigid structure, typically being constructed of a transparent, inelastic polymer such as polycarbonate, polyethylene terephthalate (PET), polyvinyl chloride, polyurethane, nylon or similar material. Such rigid or semi-rigid structure may be sealed and filled with a transparent gas or liquid to permit viewing, Alternatively, the tip may be formed of an elastic material, such as silicone rubber, polyisoprene, or polyurethane, and it may be inflatable with a transparent gas or liquid to form an expanded balloon.

The catheter body may be constructed of a flexible polymer such as polyurethane, polyvinyl chloride, PET, nylon or similar material, or it may be formed of a composite structure to impart reinforcement against bending or kinking. The catheter shaft may incorporate metallic spiral reinforcement, or a braid of polymer or metallic fibers to transmit torque along its length, and to allow for rotational oscillation (reciprocal rotation) as it navigates through the tortuous fallopian tube. The working length of the catheter will be approximately 35-40 cm, to allow the transparent tapered tip to travel the typical 10 cm length of the fallopian tube distal to the end of the cannula. A proximal portion of the catheter referred to elsewhere herein as an extension, may have a length of approximately 15-30 cm and may be bonded to an outer section of stainless-steel tube, rendering the entire proximal portion rigid. Providing a rigid proximal extension and limiting the flexible length of the tapered-tip catheter to approximately 10 cm provides a catheter structure with sufficient column strength and torque control to advance and rotationally oscillate the catheter through the fallopian tube lumen, as described in detail elsewhere herein. The rigid proximal portion also provides structure for transmitting forces to the catheter for both axial advancement and rotational oscillation, as described in detail elsewhere herein.

In an exemplary embodiment, a circumferential fabric gauze cuff, typically having a length in a range from 0.5-1.5 cm, is attached to a distal end of the viewing catheter, typically being located immediately proximal to the transparent tapered tip. The gauze cuff serves as a mechanism for cell collection, as the endoscopic catheter advances the length of the fallopian tube. The interstices of the gauze cuff retain endothelial fallopian tube cells. Cell collection is assisted by reciprocal rotation of the cuff during catheter advancement and withdrawal. The gauze cuff may be constructed of a material such as silk, cotton or polyester, with a thickness of approximately 0.5 mm. Following advancement of the catheter the length of the fallopian tube, the falloposcope device is removed from the patient, and the distal tip of the catheter containing the gauze cuff is detached or severed and submitted for cell analysis.

In an exemplary embodiment, a handle on a proximal end of the cannula incorporates a mechanism for axially advancing and simultaneously rotationally oscillating the transparent tapered tip catheter while maintaining a stationary CMOS-chip endoscope. The handle may contain a trigger that is squeezed to drive a ratchet mechanism that advances an elongated toothed plate in a forward direction. A locking mechanism is provided to prevent the elongated toothed plate from moving in a backward direction. This locking mechanism may consist of a spring loaded tooth that engages the elongated toothed plate, with the tooth angled in a position to allow the plate to advance in a forward motion only. The lock may contain an actuator to allow it to release from engagement with the elongated toothed plate, to allow insertion or retraction of the toothed plate. Reciprocal bidirectional rotation of the catheter is performed during its advancement. The catheter is attached to a rigid tube that is activated by an actuation mechanism in the handle. The surface of the rigid tube may contain axially oriented splines or a frictional outer surface; for example, a textured or an outer coating of elastomer such as silicone rubber. The rigid tube may be attached to the elongated toothed plate in a fashion that allows the tube to rotate radially with respect to the plate. For example, open end caps on the elongated toothed plate may constrain the proximal and distal ends of the rigid tube while permitting it to rotate. A stepper motor attached to the handle may rotate a wheel or a gear that contacts the splined rigid tube. The surface of the wheel that contacts the rigid tube may contain a textured surface or an elastic coating to increase contact friction. As the handle trigger is depressed, the toothed plate and attached splined tube are advanced forward, while the splined tube rotates bi-directionally as driven by the stepper motor. Alternative means of accomplishing tube rotation may be used. For example, reciprocal rotation may be accomplished by using two electromagnets coupled to the shaft of the catheter that are activated in turn to cyclically angle the catheter in the left and right directions towards ferromagnetic strips residing on the inside of each handle half. A third mechanism for achieving bi-directional catheter rotation is the use of a rigid tube containing a sinusoidal shaped slot in its bottom aspect rotatably attached to a toothed plate containing a straight slot in its central portion, and a pin fixed to the handle that protrudes through the slot in the toothed plate and the sinusoidal slot in the rigid tube. Advancement of the toothed plate with its attached rigid tube with respect to the fixed pin causes the rigid tube to oscillate in a cyclical clockwise and counterclockwise rotational fashion as the sinusoidal groove rides along the rigid pin.

Force limitation is provided to limit the force exerted at the distal tip of the catheter. During advancement of the balloon catheter through the fallopian tube, if the transparent tapered tip exceeds a preset amount of contact force against the inner wall of the tube, the force limiter will prevent additional catheter advancement. This will prevent potential tubal perforation. Force limitation of catheter advancement may be performed via magnetic coupling of the ratchet drive mechanism. The handle trigger may contain a magnet that couples with a second magnet or a ferromagnetic disc attached to the toothed drive unit that interfaces with the elongated toothed plate. As the trigger is depressed to drive the catheter forward, excessive force exerted by the transparent tapered tip against fallopian tube tissue causes the magnetic interface to decouple and release. The strength of the magnetic coupling may be adjusted to yield the degree of force limitation desired. Catheter force limitation may alternatively be provided by addition of a compression spring to the trigger drive mechanism in the falloposcope device handle. At the upper limit of desired catheter tip force, the trigger compresses the spring rather than driving the toothed plate forward.

The handle houses the electronic components used to process a video signal generated by an electronic imaging element, such as a CMOS chip, position inside of or adjacent to the conical catheter tip. The imaging element is provided as part of a separate "micro-endoscope" which incorporates the CMOS or other electronic imaging element. Power is supplied to the CMOS chip or electronic imaging element by a conductive cable that extends the length of the catheter proximally to the control circuit board in the falloposcope device handle. The video signal obtained by the imaging element is transmitted via a second cable that lies coaxially to the power cable the length of the catheter. The coaxial power and signal transmission cables may be tightly bound by an outer sheath of a polymeric material such as polyethylene terephthalate (PET) heat shrink tubing, or a spiral wound coil of flat stainless steel or other metallic foil plus an outer sheath of PET heat shrink. The coaxial conductive cables plus the spiral wound coil and outer sheath have a combined outer diameter that is smaller than the inner diameter of the catheter, allowing the CMOS chip to remain stationary as the transparent tapered tip and catheter are reciprocally rotated. In addition, torsional stability is conferred to the coaxial conductive cables by the spiral wound coil and outer sheath, to prevent CMOS chip rotation, providing a stable video image. In other instances, instead of a CMOS video chip, the imaging element may be an optical fiber with a distal lens oriented to view within the transparent tapered tip which transmits the optical image to an imaging circuitry within the handle.

A video monitor is integrated into the handle, and this monitor may pivot in the axial direction to allow the physician to concurrently view the video image as well as patient anatomy.

Application of the oscillating endoscopic catheter to cannulation of the fallopian tube has been described in detail. The principle of employing bi-directional reciprocal rotation of a transparent tapered tip endoscopic catheter with advancement force limitation may also applied to other anatomic structures involving delicate tubular ducts or vessels within the body. For example, the oscillating endoscopic catheter may be advanced through the operating channel of a cystoscope, rather than the angled 4 mm diameter cannula, and the oscillating transparent tapered tip catheter advanced in a retrograde fashion through the length of the ureter, to dislodge impacted renal stones, or to dilate ureteral strictures. Another version of the device may be advanced through the operating channel of a duodenoscope and used to cannulate the pancreatic duct or the cystic duct, to dilate strictures in the ducts or to dislodge impacted gallstones. Other versions of the oscillating transparent tapered tip endoscopic catheter may be applied to blood vessels such as arteries or veins, to recanalize occlusions due to thrombus or atherosclerotic disease. Occlusions in arteriovenous grafts used for vascular access in renal dialysis may similarly be addressed. Recanalization of occluded tubular device implants may also be performed using the oscillating endoscopic catheter. Ventriculoperitoneal shunts are placed in the treatment of hydrocephalus, and these shunts often occlude over time. An oscillating transparent tapered tip endoscopic catheter may be inserted laparoscopically to cannulate the length of a ventriculoperitoneal shunt and clear occlusions within the shunt.

The oscillating endoscopic catheter may serve as an access device to deliver an intraluminal stent or an intraluminal implant. The gauze cuff of the described device may be replaced with a self-expanding vascular stent that is deployed following recanalization of an arterial or venous occlusion using the transparent tapered tip catheter of the falloposcope or other endoscopic catheter assembly of the present invention. The oscillating endoscopic catheter may be used to perform sinoscopy, traversing strictures in the nasal sinuses, and delivering bio-absorbable stents to correct occlusive strictures. Ureteral stents may also be placed via the device.

In a first aspect, the present invention provides a falloposcope intended for use with a hysteroscope or other uterine endoscopic access device. The falloposcope comprises a cannula having an angled tip oriented to engage a fallopian tube os when the cannula is transcervically introduced to a patient's uterus, typically through the hysteroscope. The catheter has a distal viewing tip configured to be advanced from a distal end of the cannula into the patient's uterus through a cervical os. A viewing chamber has a wide proximal end attached to the distal viewing tip of the catheter, and the viewing chamber is at least partially transparent and typically tapers in a distal direction to provide a clear viewing zone for the endoscope as well as atraumatic advancement into the fallopian tube.

In particular embodiments, the viewing chamber may be fully transparent, may be comprise a pre-shaped inflatable or other shell, and/or may comprise a pre-shaped conical shell with a narrow tip configured to allow atraumatic advancement through a lumen of the fallopian tube while also providing clear view of the luminal wall as it is separated by the conical surface. In a specific instance, the catheter may have a diameter in a range from 0.75 mm to 1 mm, the base of the pre-shaped shell has a diameter in a range from 1 mm to 1.25 mm, and the pre-shaped shell has a length in a range from 4 mm to 7.5 mm.

In addition to providing viewing of the interior of the fallopian tube lumen, the falloposcopes of the present invention may further comprise for cell collection, tissue sampling, biopsy, or other diagnostic procedures. For example, a fabric (gauze) cuff, brush, or other cell collection element located on an exterior of the catheter, typically being immediately proximal of the viewing chamber.

The falloposcopes of the present invention will typically include a handle attached to a proximal end of the cannula where the handle is configured to distally advance the catheter from the distal end of the cannula. The handle typically comprises a drive assembly configured to simultaneously advance and rotationally oscillate the catheter. For example, the drive assembly may comprise a trigger coupled to a ratchet mechanism which incrementally advances the catheter. The drive assembly typically further comprises a mechanism for rotationally oscillating the catheter. In one instance, the mechanism comprises a motor-driven rocker arm that engages and rotationally oscillates the catheter or an extension of the catheter. Alternatively, the mechanism comprises a pin fixed in the handle, wherein the pin tracks in a sinusoidal, zig-zag, or other serpentine groove formed in an exterior surface of the catheter or an extension of the catheter to cause the catheter to rotationally oscillate as the catheter is advanced by the trigger and ratchet. Further alternatively, the catheter may be caused to rotationally oscillate by coupling a pair of laterally adjacent electromagnets to the catheter or an extension thereof. By providing ferromagnetic strips on opposed sides of the handle, and alternately energizing the two magnets, the catheter can be alternately rotated in opposite rotational directions.

In a second aspect, the present invention provides a method for accessing a patient's fallopian tube. The method comprises transcervically introducing a distal end of a cannula into the patient's uterus to engage the patient's fallopian tube os. A catheter having a distal viewing tip is advanced from a distal end of the cannula into the patient's fallopian tube through the patient's fallopian tube os. The catheter is then atraumatically advanced through the patient's fallopian tube while viewing an interior of the fallopian tube through a tapered viewing chamber attached to the distal viewing tip of the catheter.

In particular instances of the methods of the present invention, the viewing chamber has a wide proximal end attached to the distal viewing tip of the catheter and the viewing chamber is at least partially transparent and tapers in a distal direction to provide both a clear viewing zone for the endoscope and atraumatic advancement into the fallopian tube. The viewing chamber is typically fully transparent and may comprise a pre-shaped shell which may further be conical in shape. In specific instances, the catheter may have a diameter in a range from 0.75 mm to 1 mm, the base of the pre-shaped shell has a base diameter in a range from 1 mm to 1.25 mm and a length in a range from 4 mm to 7.5 mm when inflated.

The methods will often further comprises diagnostic testing, such as cell collection, tissue collection biopsy, and the like. In particular the catheter may be used to collect and withdraw cells from the fallopian tube, for example by engaging a cell collecting surface on an exterior surface of the catheter against an inner wall of the fallopian tube. In specific instances, engaging a cell collecting surface comprises rotationally oscillating the catheter, typically while incrementally advancing the catheter using translating a ratchet mechanism.

DETAILED DESCRIPTION OF THE INVENTION

Figures 1A, 1B:
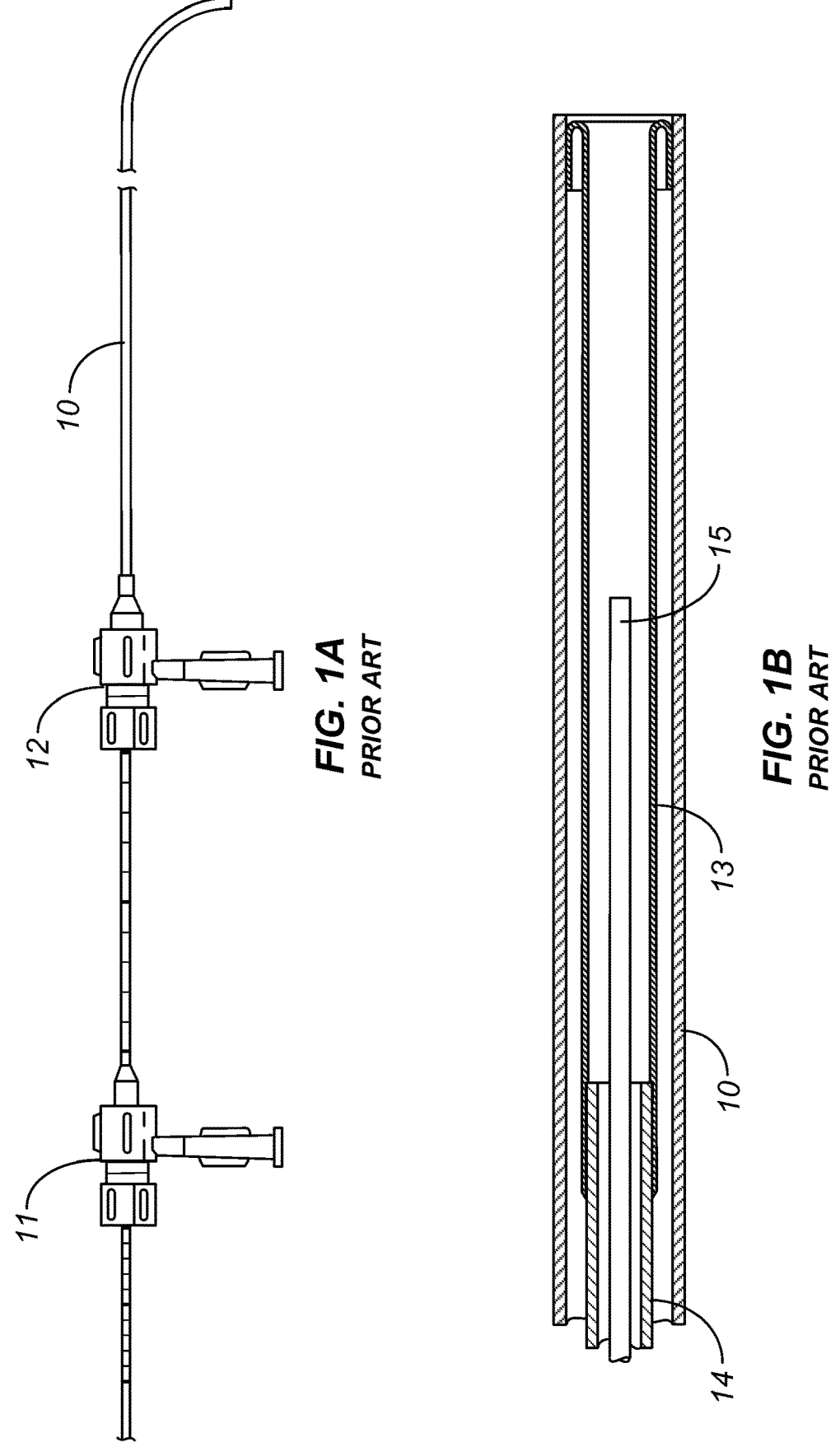
FIGS. 1A-1B show the elements of a prior art linear everting balloon catheter used to perform falloposcopy.

FIG. 1A shows a previous catheter 10 used for falloposcopy. The catheter 10 everts a balloon 13 from its distal end through the fallopian tube and uses the everting balloon to deliver an endoscope into the fallopian tube. Catheter 10 is pressurized with saline, and manual advancement of proximal connector 11 towards distal connector 12 everts a balloon from distal tip of catheter 10. FIG. 1B is a cross-sectional view of the distal portion of catheter 10 illustrating the distal rolled over end of inverted balloon 13 attached to the inner wall of the distal end of catheter 10, and the proximal end of inverted balloon 13 attached to the distal end of inner catheter 14. Endoscope 15 lies inside inner catheter 14 and inverted balloon 13.

Figure 2:
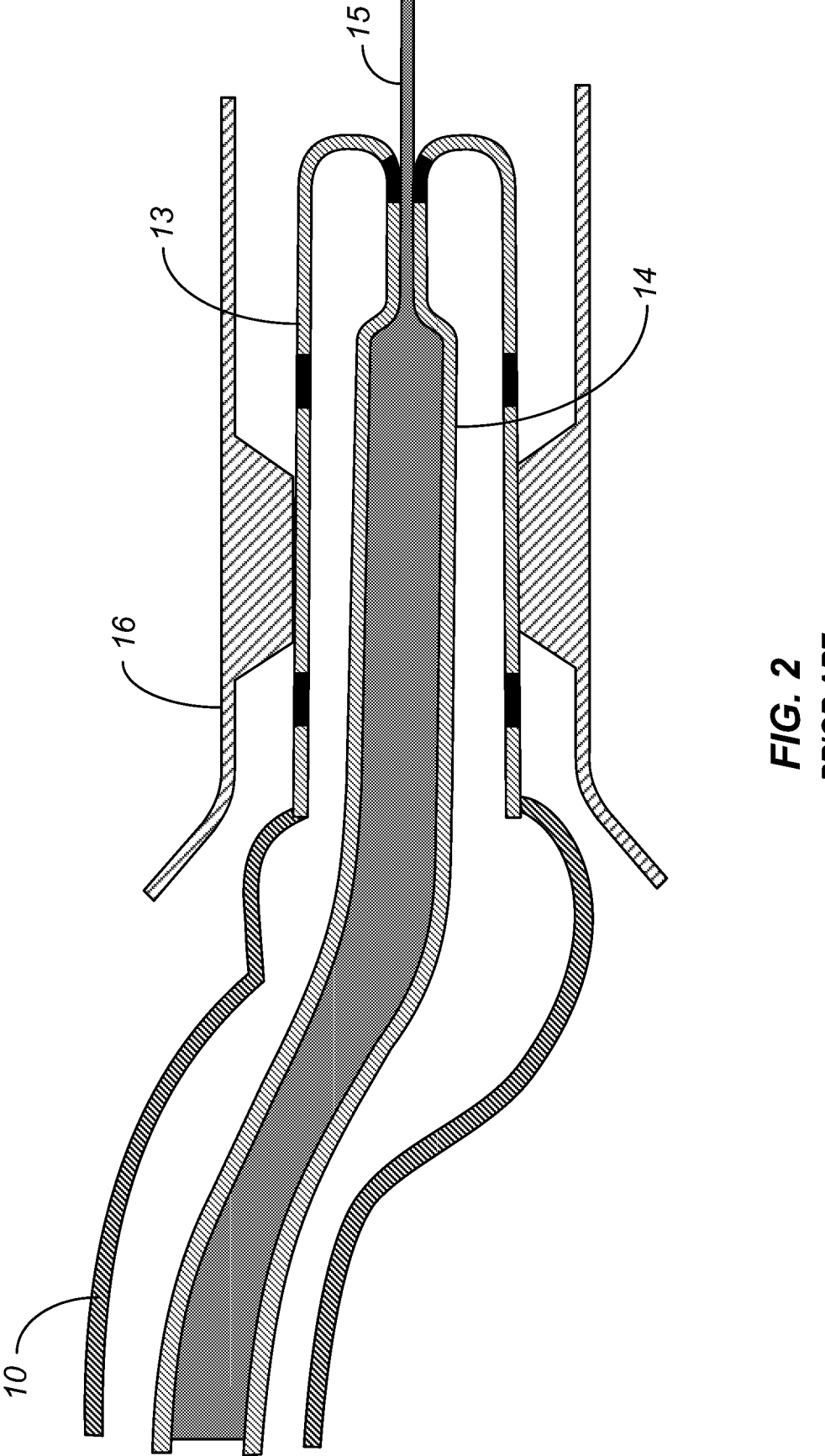
FIG. 2 illustrates eversion of the prior art balloon of FIG. 1 with the endoscope extending past the everting balloon.

FIG. 2 depicts a linear everting balloon catheter 10 everting balloon 13 through fallopian tube 16. During the eversion process, balloon 13 assumes a double-walled, toroidal configuration, compressing endoscope 15 and driving it forward at twice the rate of the advancing balloon 13. The exposed endoscope 15 may be driven into the wall of fallopian tube 16, causing dissection or perforation. Therefore, falloposcopy with the linear everting balloon catheter 10 is performed in increments, with eversion halted after a short distance to depressurize catheter 10 and allow endoscope 13 to be pulled back into the everting balloon 13 and inner catheter 14.

Figure 3:
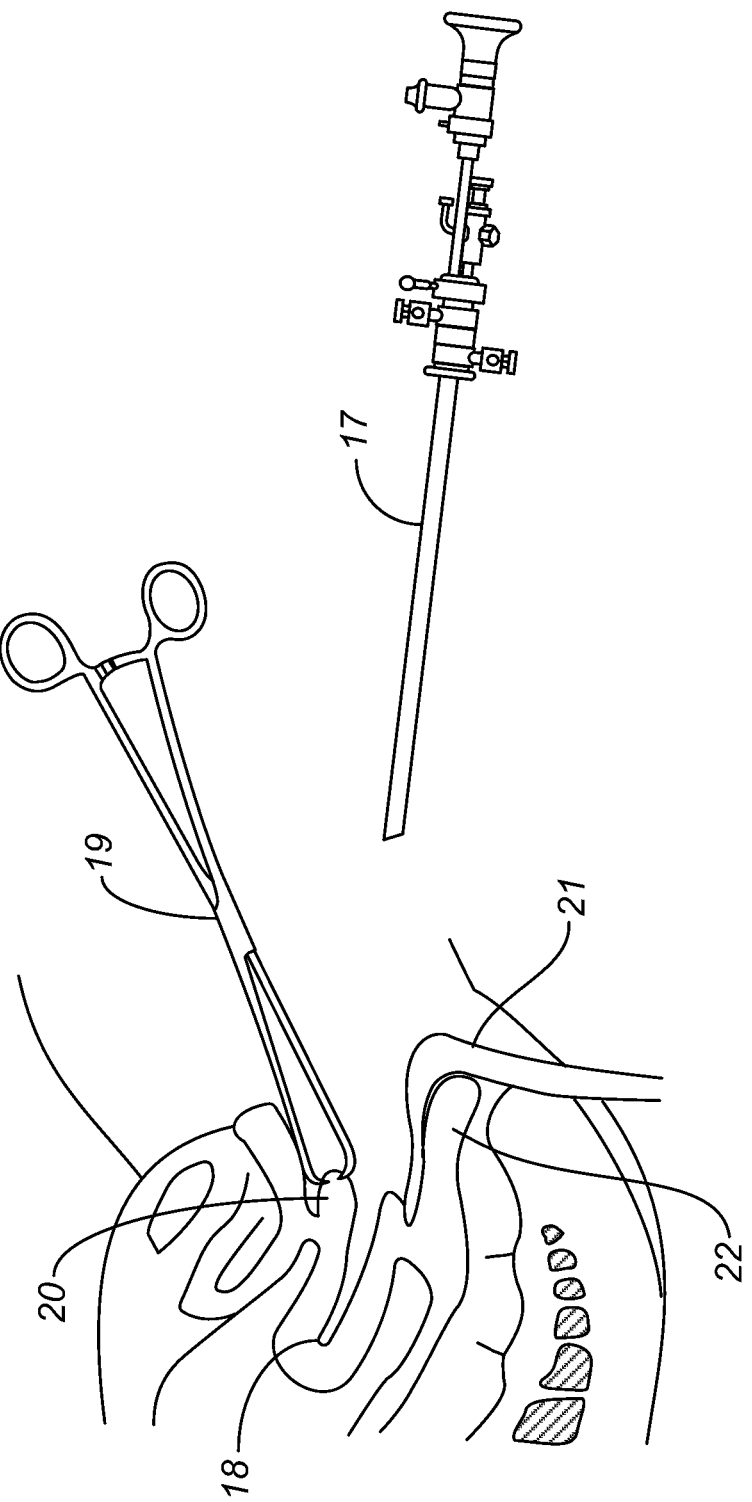
FIG. 3 shows the pointed tips of the tenaculum forceps used to manipulate the cervix during insertion of a conventional rigid hysteroscope.

FIG. 3 shows the instrumentation required to perform hysteroscopy with a rigid hysteroscope 17. fallopian tube catheterization is also performed by insertion of guidewires and catheters through the operating channel of hysteroscope 17 into the fallopian tube. In order to insert a rigid 5 mm or 7 mm diameter hysteroscope 17 into the uterus 19, the sharp pointed distal tips of a tenaculum forceps 19 is used to grasp and manipulate the cervix 20 during introduction of hysteroscope 17 into the uterus 19. Tenaculum forceps 19 application is extremely painful, and generally requires anesthesia, including sedation and injection of local anesthesia such as Lidocaine in the paracervical area. A vaginal speculum 21 is also generally used to retract vaginal tissue 22 during hysteroscopy. Vaginal speculum 21 application is tolerated to a greater degree by the patient, and its use is a component of the annual pelvic examination conducted for the Pap smear performed for the diagnosis of cervical malignancy.

Figure 4A:
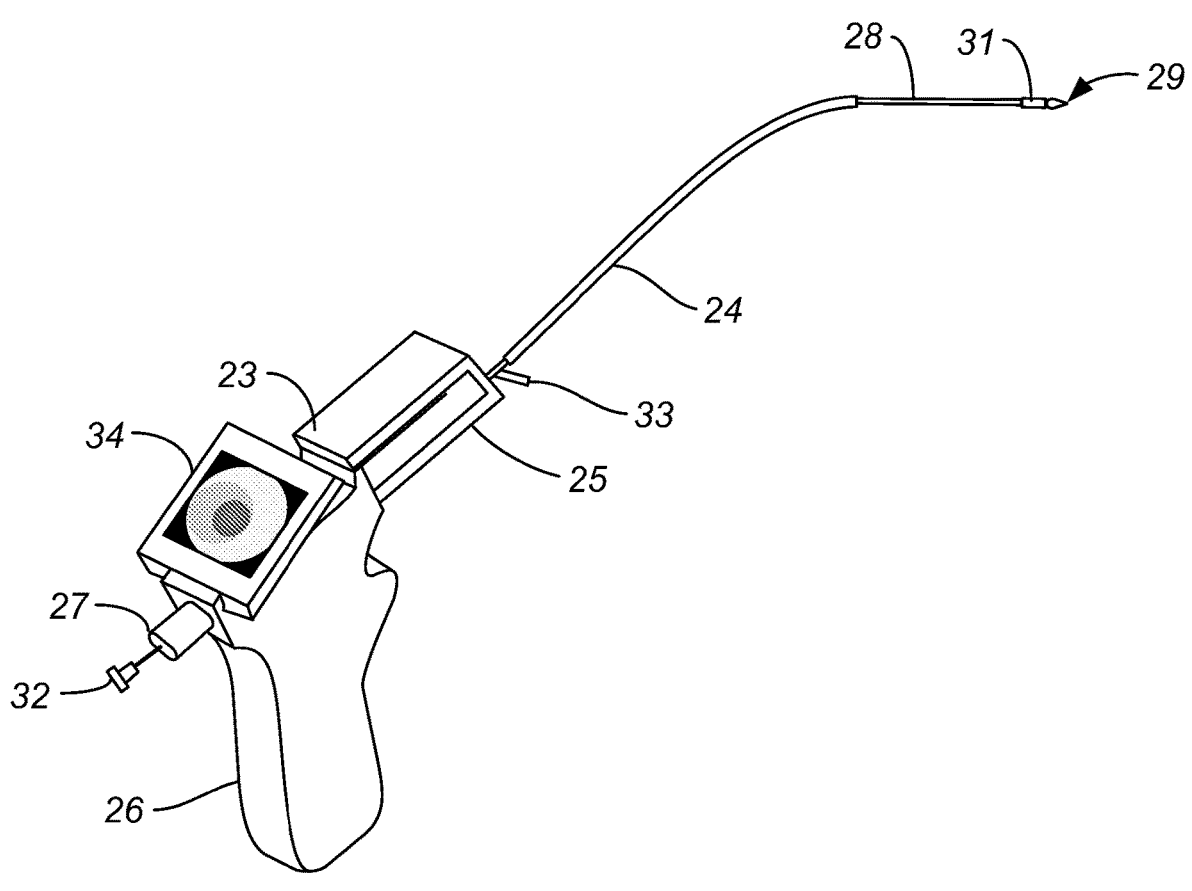
FIGS. 4A-4B show the configuration of an oscillating endoscopic catheter of the present invention, referred to herein as a falloposcope, for fallopian tube cannulation.
Figure 4B:
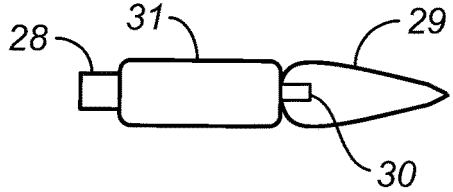

FIG. 4A depicts the falloposcope device 23 of the present invention configured to navigate the length of the fallopian tube in the setting of a physician's office without causing patient pain or injury to the patient's fallopian tube. The falloposcope device 23 includes a cannula 24, typically a rigid cannula, of approximately 4 mm in outer diameter, with an angled distal end. The cannula 24 is attached to an extension 24a extending distally from the device handle 26. Device handle 26 contains a video display 34 on its proximal aspect, to allow the physician to view the endoscopic image. The inside of device handle 26 contains a motorized drive system that reciprocally rotates a splined tube 28a attached to a catheter 28 that lies inside the lumen of rigid cannula 24. A transparent tapered tip 29 is attached to the distal end of catheter 28. The transparent tapered tip 29 and catheter 28 may be activated by the motor drive in handle 26 to perform reciprocal clockwise and counter-clockwise rotation with a sweep arc of up to 180° at a frequency of approximately 2-5 cycles per second. Infusion ports 32 and 33 may be connected to allow fluid injection through device 23. Infusion port 32 may incorporate a check valve that allows inflation of transparent tapered tip 29 via catheter 28 if transparent tapered tip 29 is an inflatable elastic or inelastic balloon. Injection port 33 may allow fluid infusion via rigid cannula 24 for uterine distention for improved visualization of the os of the fallopian tube for cannulation by transparent tapered tip 29. FIG. 4B is an enlarged view of the distal tip of the falloposcope device 23, showing the transparent tapered tip 29 attached to the distal end of catheter 28. Catheter 28 has an outer diameter of approximately 0.8 mm, and transparent tapered tip 29 has a maximum outer diameter of approximately 1.1 mm, and a length of approximately 5-10 mm. The distal tip 30 of a CMOS chip endoscope extends into the proximal portion of transparent tapered tip 29, allowing visualization of the cervix, uterus and fallopian tube as the falloposcope device 23 is advanced into position in the fallopian tube os, and visualization of the fallopian tube as the catheter 28 is advanced the length of the fallopian tube. The tapered configuration of transparent tip 29 serves to retract the walls of a non-distended fallopian tube as the catheter 28 is advanced forward out of cannula 24. The distal end of cannula 24 remains outside of the fallopian tube os. A gauze or other fabric cuff 31 is attached to the distal end of catheter 28, immediately proximal to transparent tapered tip 29. The interstices of gauze or other fabric cuff 31 allow it to sample and retain endothelial cells from the fallopian tube during insertion and removal of catheter 28.

Figures 5A, 5B:
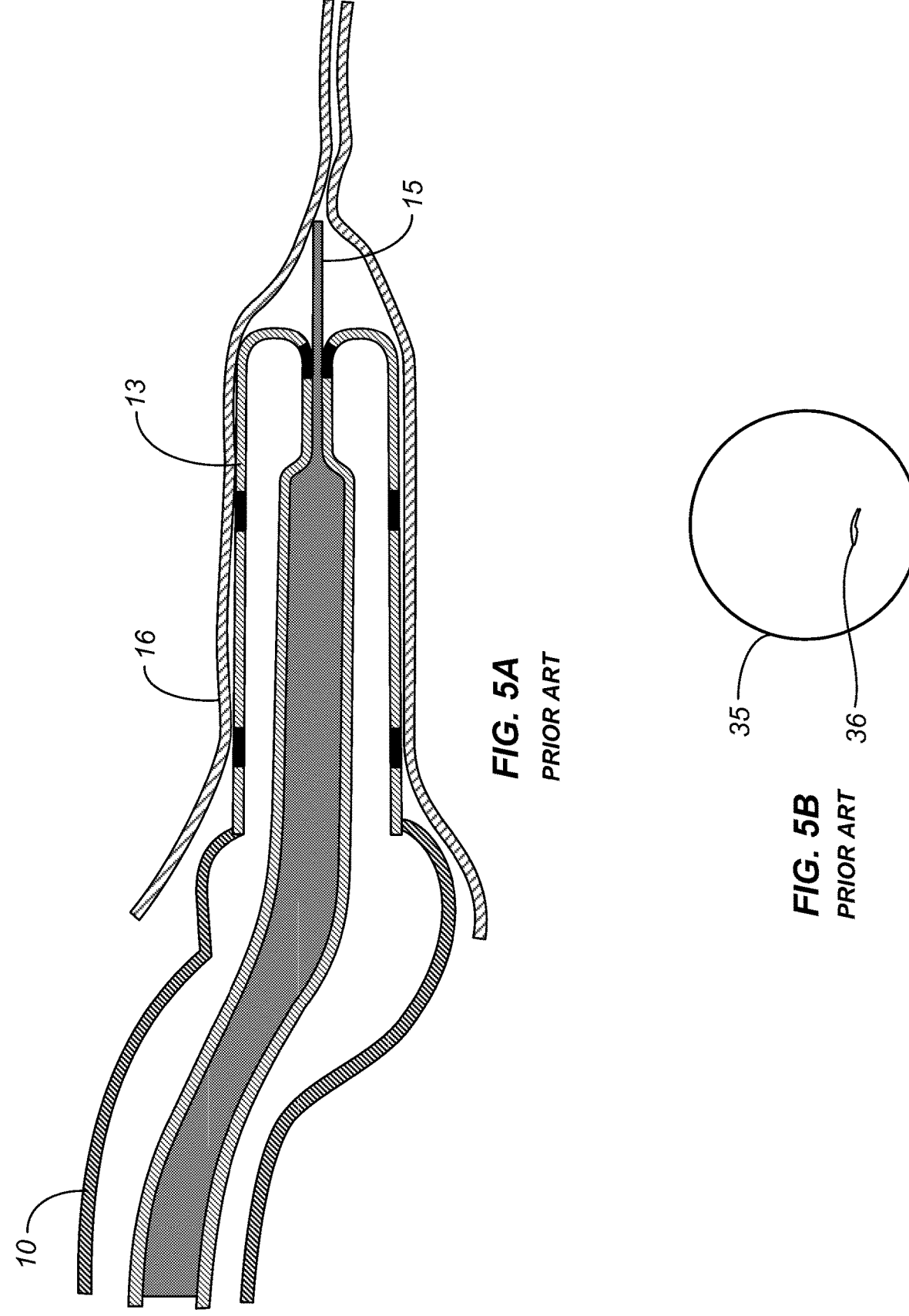
FIGS. 5A-5B show the inability for a prior art endoscope deployed by a linear everting balloon catheter to visualize the lumen of a non-distended fallopian tube.

FIG. 5A illustrates that with the advancement of a conventional endoscope 15 from a prior art linear everting balloon 13, the tip of endoscope 15 lies against tissue of a collapsed fallopian tube 16 prevents visualization of the fallopian tube lumen. FIG. 5B shows the resultant endoscopic image 35 with a barely perceptible collapsed lumen 36. With such limited imaging, continued endoscope advancement upon balloon eversion is at risk of causing tubal perforation.

Figure 6A:
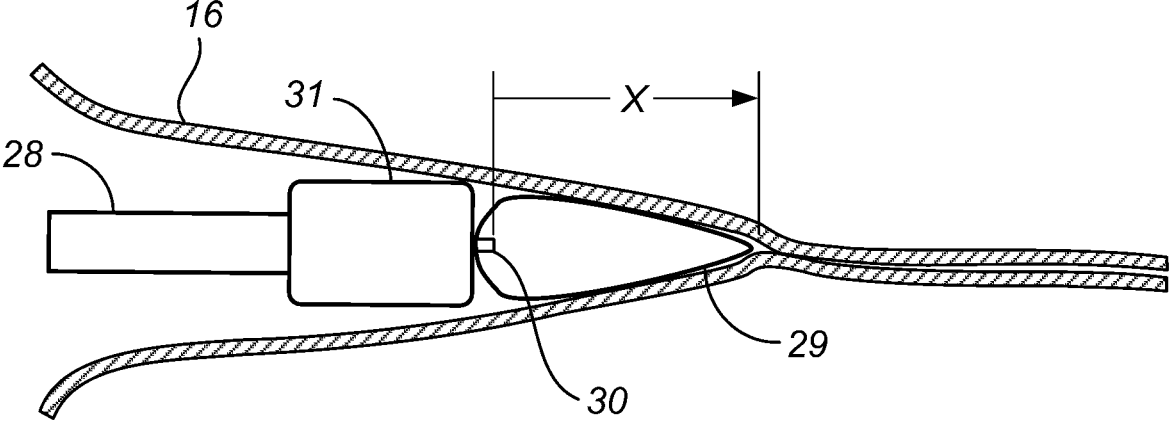
FIGS. 6A-6B illustrate the advancement of a transparent tapered tip of the falloposcope of the present invention showing distention of the fallopian tube during its advancement to enhance visualization of the fallopian tube lumen.
Figure 6B:
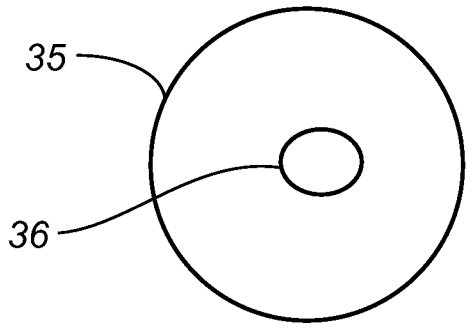

FIG. 6A illustrates advancement of the transparent tapered tip 29 on the distal end of catheter 28 inside a collapsed fallopian tube 16. The transparent tapered tip 29 distends fallopian tube 16, and since the transparent tapered tip 29 extends a distance "X" distal to the tip 30 of CMOS chip endoscope, it provides a viewing length of approximately 7 mm of fallopian tube lumen. FIG. 6B shows the corresponding endoscopic image 35, now with a clearly visualized patent lumen 36. The transparent tapered tip 29 may now be advanced into tubal lumen 16 with a reduced risk of perforating the wall of fallopian tube 16.

Figure 7:
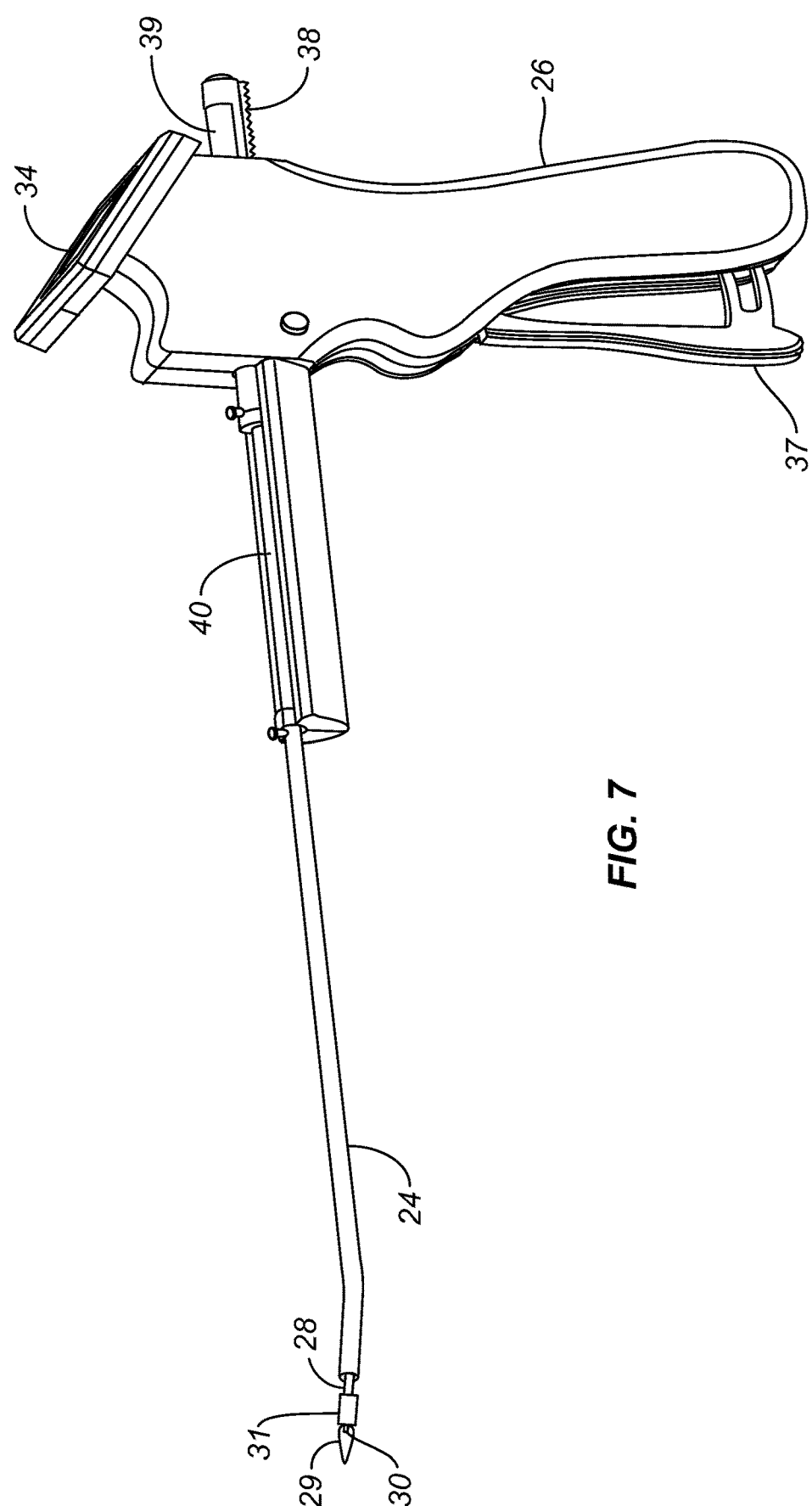
FIG. 7 shows an embodiment of the falloposcope of the present invention that employs a trigger handle to advance the transparent tapered tip of the falloposcope of the present invention distally.

FIG. 7 shows a configuration of the falloposcope device that employs a trigger 37 in handle 26 to advance the catheter 28. Depression of trigger 37 drives the toothed plate 38 forward. Rigid tube 40 is connected to toothed plate 38 in a fashion that allows it to rotate relative to toothed plate 38 while constrained against axial movement between them. A small diameter rigid tube 41 extends forward from rigid tube 39, and slides within the inner lumen of angled cannula 24. Catheter 28 is bonded to the inner lumens of rigid tube 40 and small diameter rigid tube 41. Rotation of rigid tube 40 causes rotation of catheter 28. A transparent tapered tip 29 is attached to the distal end of catheter 28. A microendoscope, generally a CMOS chip endoscope, extends through the lumen of catheter 28, and its distal tip 30 resides inside the transparent tapered tip 29. The video image obtained by micro endoscope is viewed on the video display 34. A gauze cuff 31 is attached to the distal end of catheter 28, immediately proximal to the transparent tapered tip 29. Gauze cuff 31 is used to collect endothelial cells from the fallopian tube as the catheter 28 is advanced and withdrawn the length of the fallopian tube.

Figure 8:
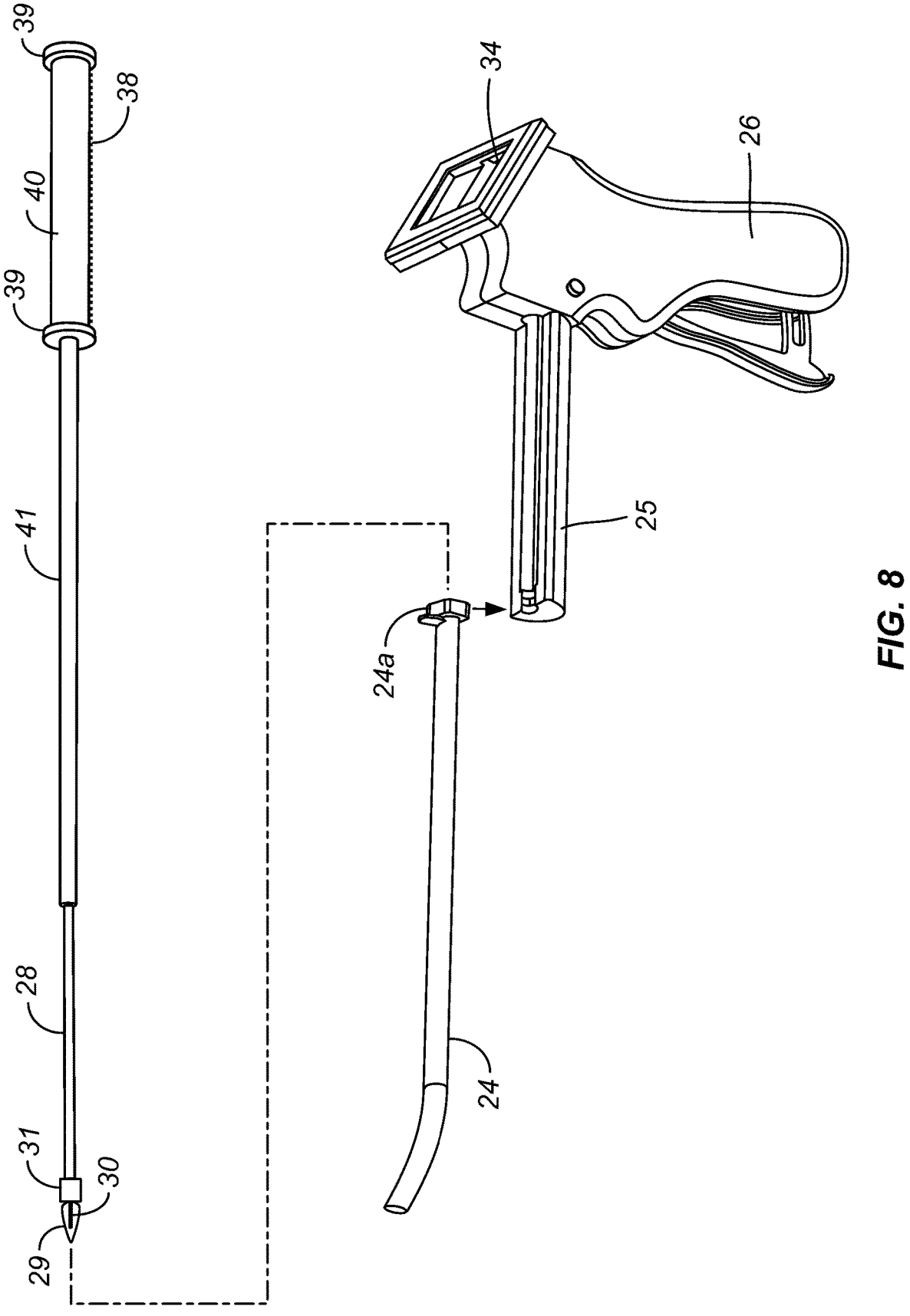
FIG. 8 is a disassembled view depicting the components of the falloposcope including a reusable handle, a disposable cannula, and a disposable catheter.

FIG. 8 is a dissembled view of the falloposcope of the present invention depicting the reusable handle 26 containing internal drive mechanisms and a video display 34. A proximal end 24a of the disposable cannula 24 removably attaches to the reusable handle 26. The catheter 28 is included as part of a disposable assembly comprising the toothed plate 38, the rigid tube 40, small diameter rigid tube 41, the transparent tapered tip 29, the gauze cuff 31, and micro-endoscope. Bearings 39 are fixed to the proximal and distal ends of toothed plate 38 to rotationally support the rigid tube 40, allowing a subassembly of the rigid tube 40, small diameter rigid tube 41, the transparent tapered tip 29, the gauze cuff 31, and micro-endoscope to rotate about their longitudinal axis relative to the toothed plate 38 and the handle 26. The subassembly is first inserted into the reusable handle 26 followed by placement of the disposable angled cannula 24 coaxially over transparent tapered tip 29, catheter 28 and small diameter rigid tube 41 into attachment with reusable handle 26.

Figure 9:
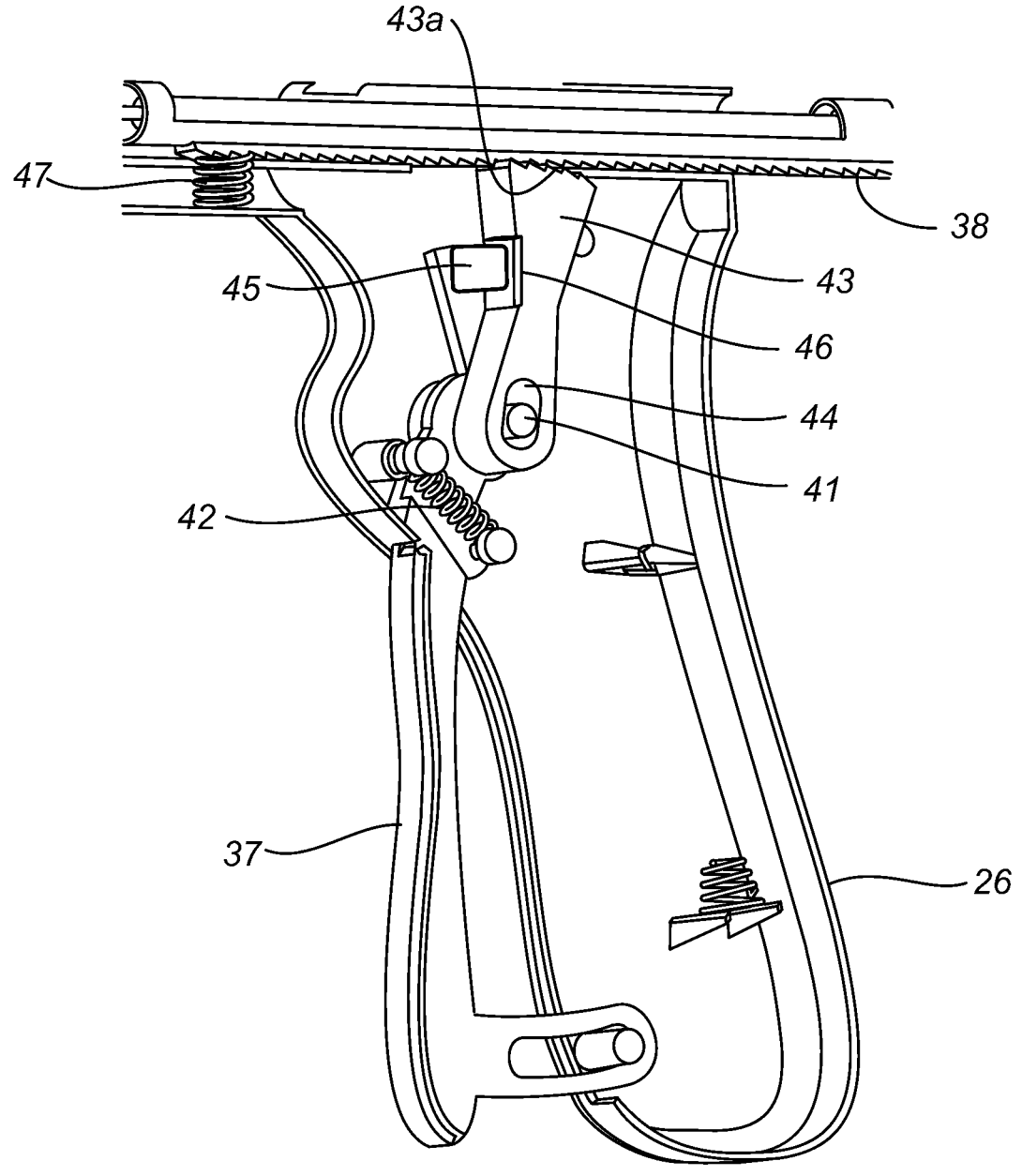
FIG. 9 shows a catheter advancement mechanism disposed in the handle and incorporating a force limiting feature.

FIG. 9 shows an embodiment of a drive mechanism incorporated inside the falloposcope device handle 26. The trigger 37 pivots on pin 41, and a tension spring 42 returns the trigger 37 to its resting position following actuation. A link 43 has an elongated slot 44 in a lower end that also pivots on the pin 41. An upper or superior edge 43a of link 43 contains teeth that mesh with the teeth 38a on a lower surface of the toothed plate 38. A magnet 45 is attached to an upper portion of trigger 37, and the magnet 45 interfaces with a ferromagnetic plate 46 attached to link 43. When trigger 37 is depressed (manually closed by a user), magnet 45 draws the toothed link 43 forward, driving toothed plate 38 forward as well. Magnetic coupling of the trigger 37 to the link 43 limits the forward driving force that can be applied to the catheter, reducing the risk of injuring the fallopian tube. That is, the forward driving force of toothed plate 38 is limited by the force of magnetic attraction between magnet 45 and ferromagnetic plate 46. The mechanism of force limitation of the catheter tip against the fallopian tube is determined by the force of magnetic coupling in the drive unit located in handle 26. The angles of the teeth in the toothed plate 38 and the link 43 are configured to yield forward directional advancement of toothed plate 38 upon depression of trigger 37. Upon release of trigger 37, tension spring 42 pulls trigger 37 forward, and retracts link 43 to its original position. The elongated slot 44 allows link 43 to drop down on pin 41 and facilitate backward movement of its superior toothed edge against the toothed plate 38. A compression spring 47 provides resistance against toothed plate 38, to prevent it from moving backward during return movement of link 43.

Figure 10A:
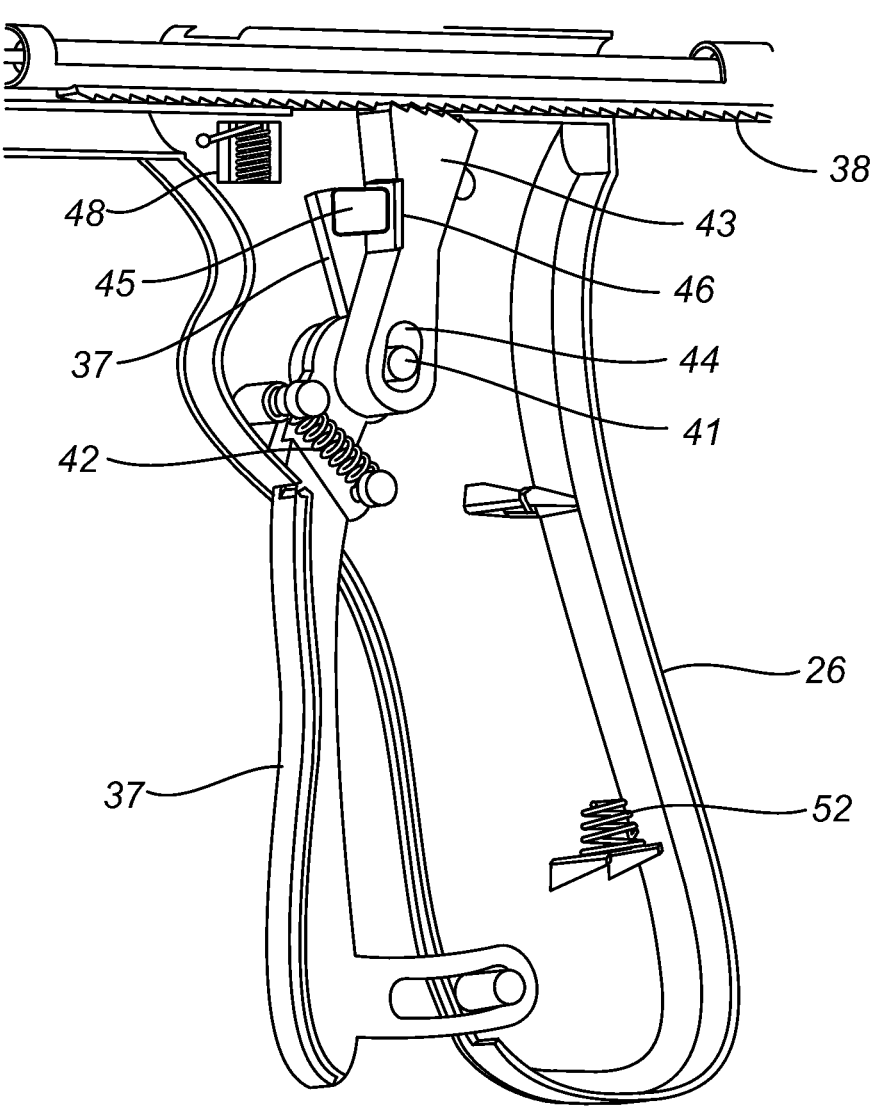
FIGS. 10A-10B show the handle mechanism incorporating a releasable lock preventing retrograde catheter movement.
Figure 10B:
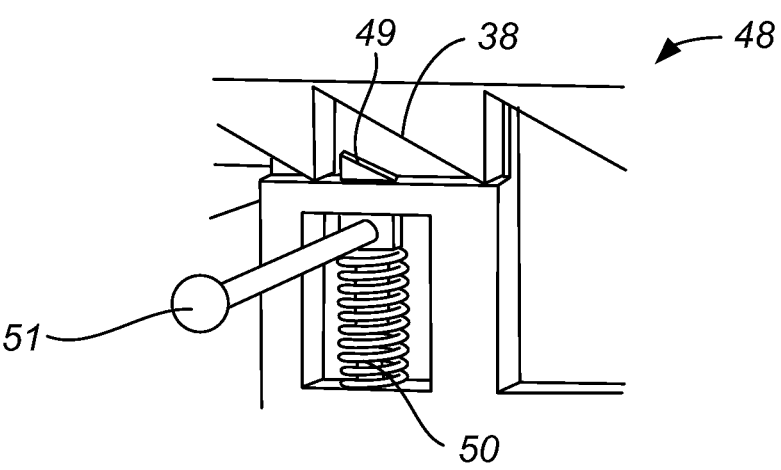

FIG. 10A shows the drive mechanism of the falloposcope device handle 26 incorporating a releasable lock 48 against toothed plate 38, to restrict it to unidirectional forward advancement. FIG. 10B is an enlarged view of releasable lock 48, illustrating its components, including a locking tooth 49 elevated by compression spring 50 to engage with a corresponding tooth of toothed plate 38. An actuator knob 51 may be depressed to disengage locking tooth 49 during insertion of toothed plate 38 into reusable handle 26 or during retraction of toothed plate 38 to retract the catheter tip.

Figure 11A:
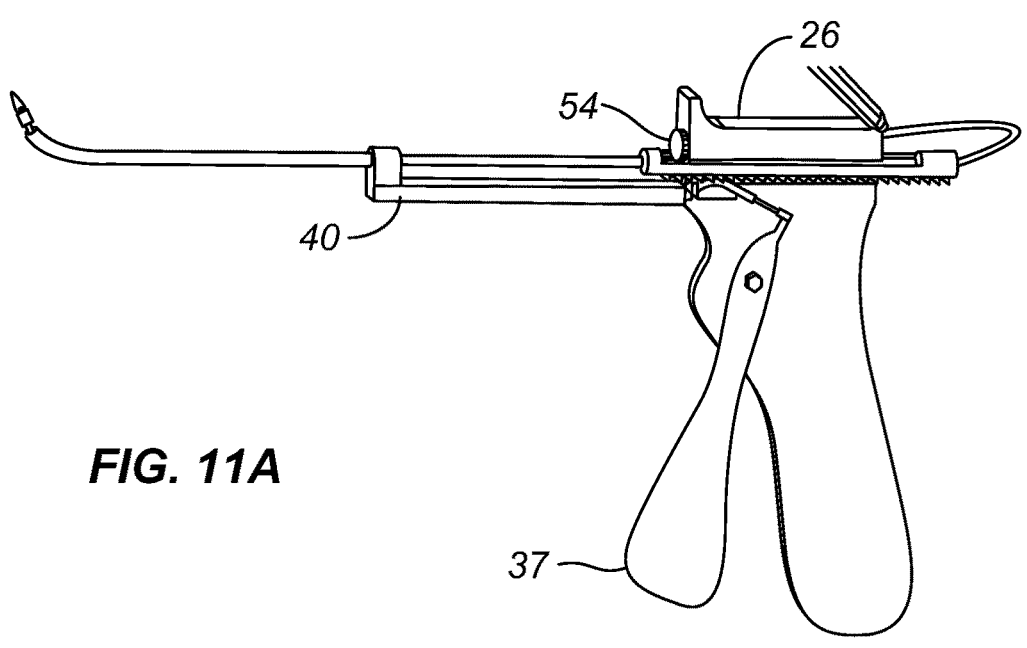
FIGS. 11A-11C show a mechanism for rotationally oscillating (reciprocal oscillating) the falloposcope of the present invention and having an alternate advancement force limitation mechanism.
Figure 11B:
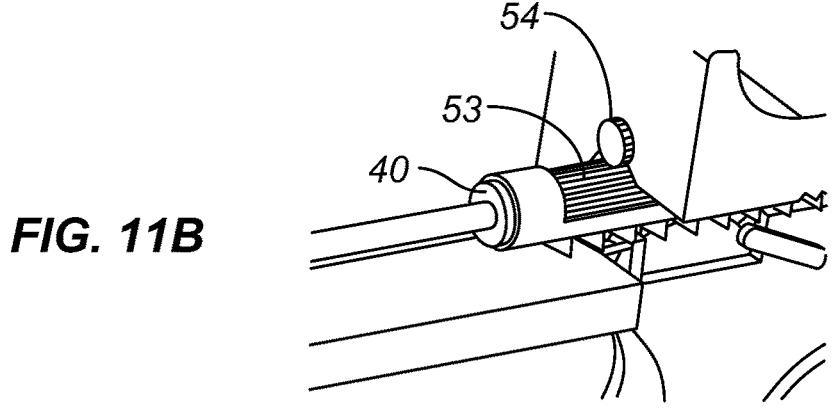
Figure 11C:
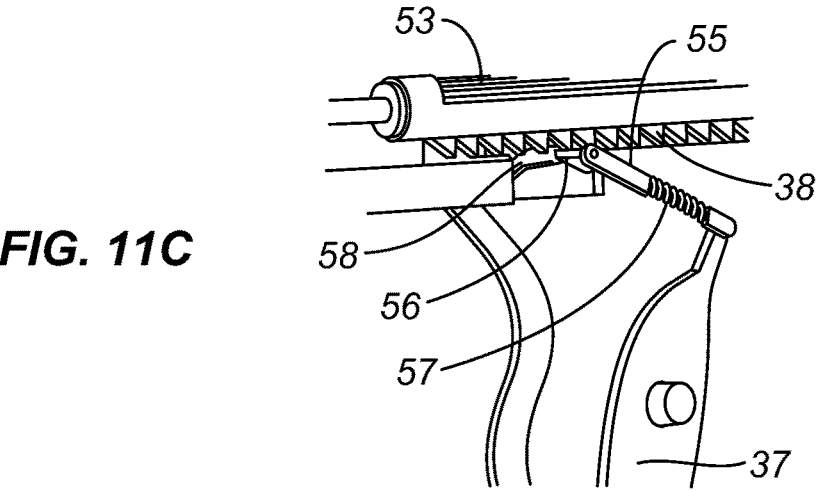

FIG. 11A illustrates an embodiment of a mechanism to achieve oscillatory catheter rotation. A stepper motor (not shown) inside reusable handle 26 has an attached gear face 54 positioned outside handle 26 that interfaces with rigid tube 40. In this embodiment, rigid tube 40 is splined, with axial gear teeth on its outer surface that match the teeth on gear face 54. FIG. 11B is an enlarged view of the motor drive mechanism, showing the drive gear 54 meshed with the spline gear 53 surface on rigid tube 40. The arc and the frequency of catheter rotation may be adjusted via electronic control parameters input to the stepper motor. FIG. 11C depicts an alternate mechanism for catheter tip force limitation. The superior portion of trigger 37 contains a linkage 55 containing a cross-pin 56 that is spring loaded via compression spring 57. The cross-pin 56 rides along an arched groove 58 and engages the teeth of toothed plate 38 to produce forward motion upon depression of trigger 37. When the maximum set catheter tip contact force is exceeded, spring 57 compresses as the trigger is pulled, preventing forward advancement of the catheter.

Figure 12A:
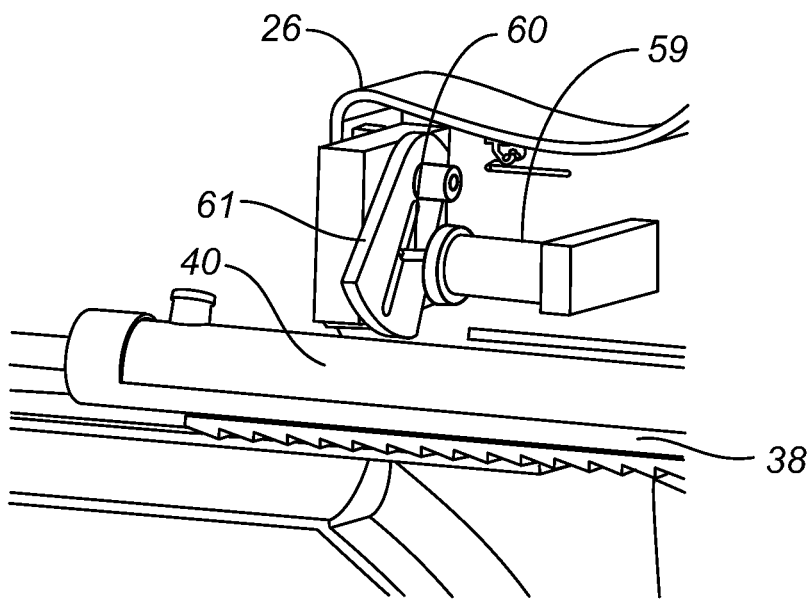
FIGS. 12A-12B show an alternate mechanism rotationally oscillating (reciprocal oscillating) the falloposcope of the present invention.
Figure 12B:
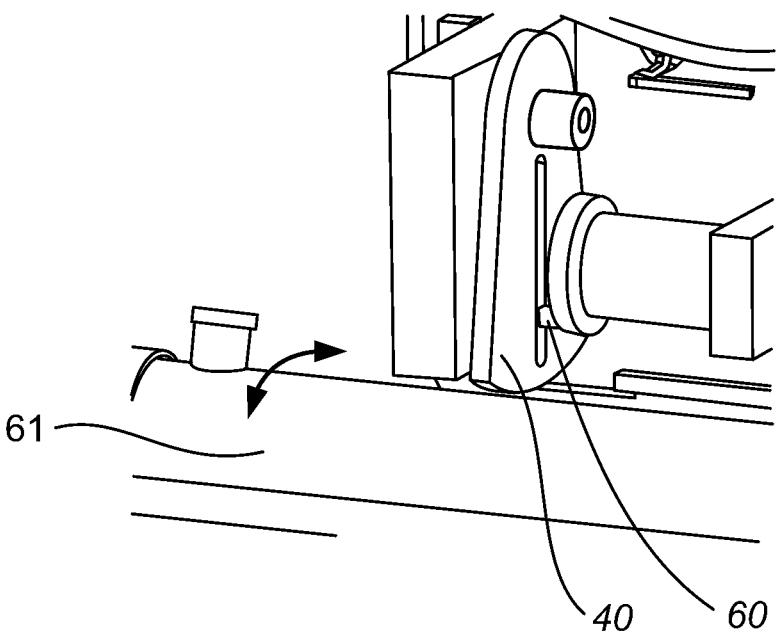

FIGS. 12A and 12B depict an alternate drive mechanism for oscillatory catheter rotation. A motor 59 is attached to the inside of the body of handle 26. The motor 59 rotates a disc that carries an offset pin 60 that circles continuously in a groove in a pivotally mounted plate 61, causing a pendulum-like motion back and forth. A bottom edge of the grooved plate 61 contacts an exterior surface of rigid tube 40. The bottom edge of grooved plate 61 contacts the exterior surface of the rigid tube 40 with sufficient friction to cause the rigid tube 40 to rotationally oscillate about its axis. The bottom edge of grooved plate 61 may be partially or wholly covered with a layer of elastomeric material, for example, silicone rubber or polyurethane, to enhance frictional contact. The surface of rigid tube may be smooth, or it may contain multiple axial grooves or other surface features or texturing if additional friction is needed for rotation.

Figures 13A, 13B:
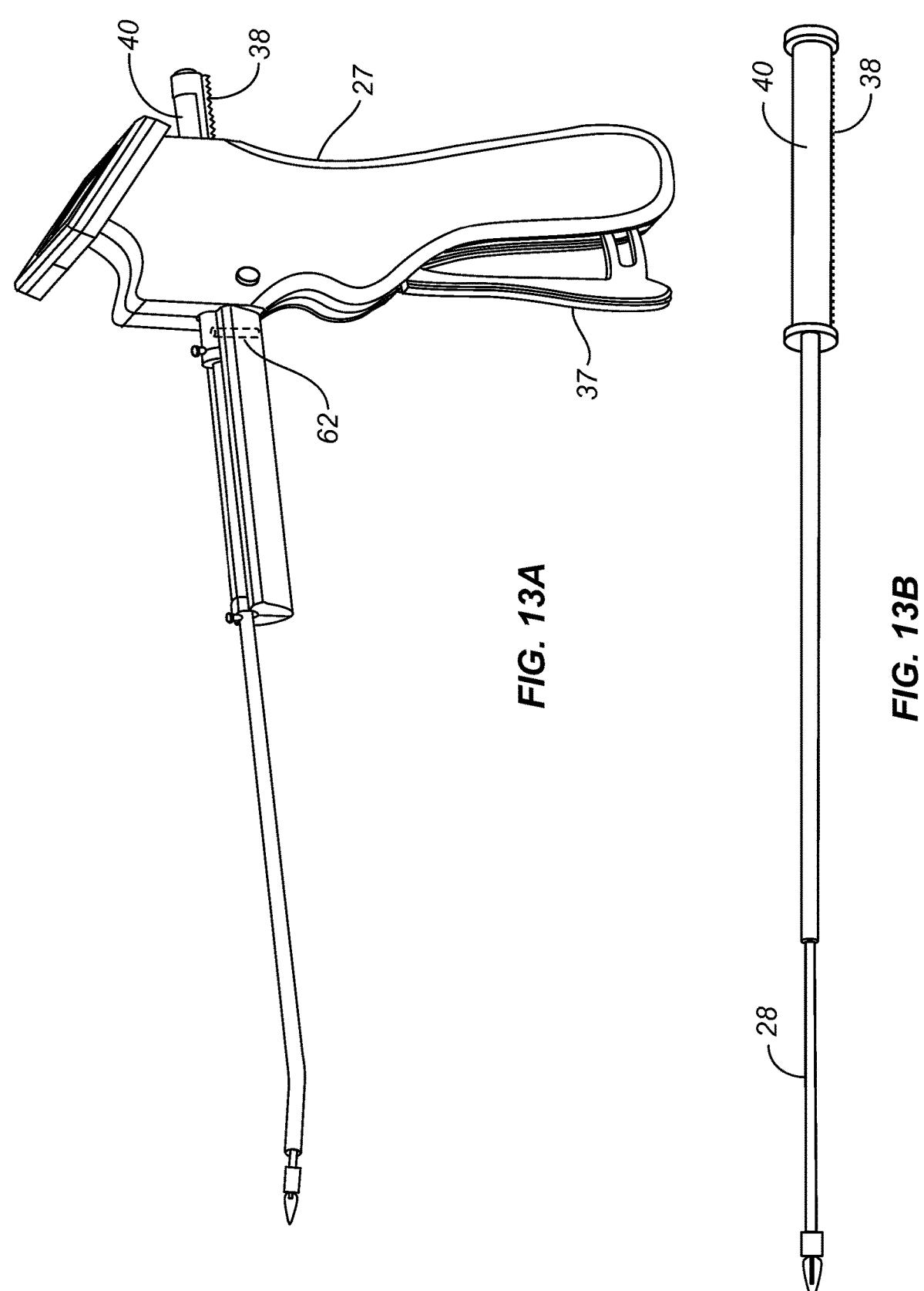
FIGS. 13A-13D show a third mechanism for rotationally oscillating (reciprocal oscillating) the falloposcope of the present invention.
Figure 13C:
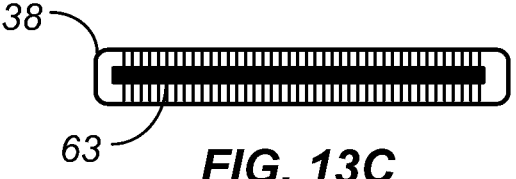
Figure 13D:
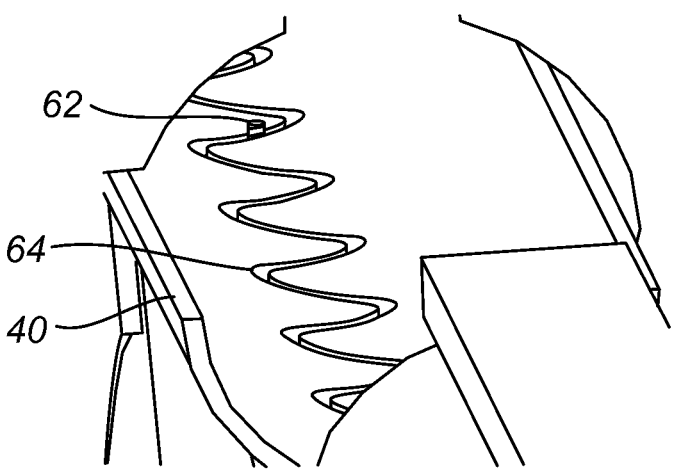

FIGS. 13A-13D a further mechanism for rotationally oscillating the catheter as it is advanced. A stainless-steel pin 62 is anchored in the body of a handle 26 (FIG. 13A). Pin 62 protrudes through slots in the toothed plate 38 on a bottom of the rigid tube 40. FIG. 13B shows the disposable catheter 28 component of the falloposcope device, including the toothed plate 38, the rigid tube 40, as also shown in FIG. 8B. FIG. 13C is a bottom view of the toothed plate 38, showing a slot 63 that extends through the full thickness of toothed plate 38. FIG. 13D is an enlarged view of a portion of the rigid tube 40, showing a sinusoidal groove 63 in the wall of rigid tube 40, and pin 62 protruding through sinusoidal groove 63. As trigger 37 is depressed to drive toothed plate 38 forward, the sinusoidal groove 64 in rigid tube 40 advances along stationary pin 62, causing rigid tube 40 to rotate in a cyclical clockwise and counterclockwise fashion.

Figures 14A, 14B, 14C, 14D:
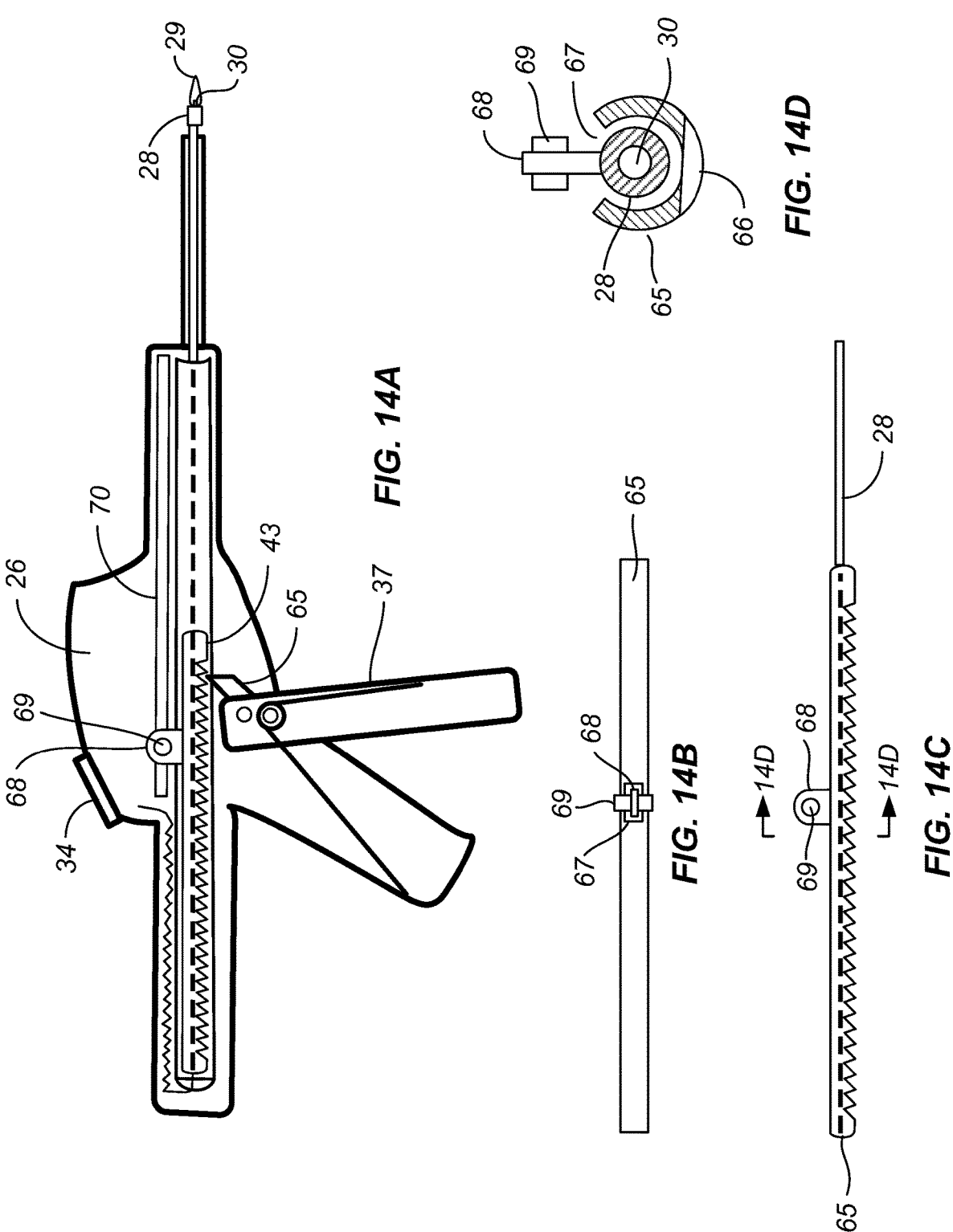
FIGS. 14A-14D depict a further alternative mechanism for rotationally oscillating (reciprocal oscillating) the falloposcope of the present invention using electromagnetic actuation.

FIG. 14A shows another embodiment of a falloposcope device with a trigger 37 that actuates a toothed link 43 to drive a toothed tubular rod 65 forward. The catheter 28 with the transparent tapered tip 29 protecting the distal tip 30 of the micro-endoscope is disposed inside the lumen of toothed tubular rod 65. A flange 68 attached to catheter 28 protrudes out of a slot 67 in the top of toothed tubular rod 65, as seen in FIG. 14B. Electromagnets 69 are attached to left and right sides of flange 68, and ferromagnetic strips 70 are attached to the left and right halves of handle 26, in apposition to electromagnets 69. As toothed tubular rod 65 is driven forward by depression of trigger 37, left and right electromagnets 69 are activated in turn to cause flange 68 to rotationally oscillate catheter 28. FIG. 14C is a side view of toothed tubular rod 65 housing catheter 28 within its lumen. FIG. 14D is a cross-section of toothed tubular rod 65 at the site of the slot 67, showing flange 65 attached to the top surface of catheter 28, and electromagnets 69 attached to the left and right surface of flange 68. Slot 67 is sufficiently wide to allow left and right-sided excursions of flange 65 to conduct a rotation of catheter 28 in an arc of approximately 120°.

Figure 15:
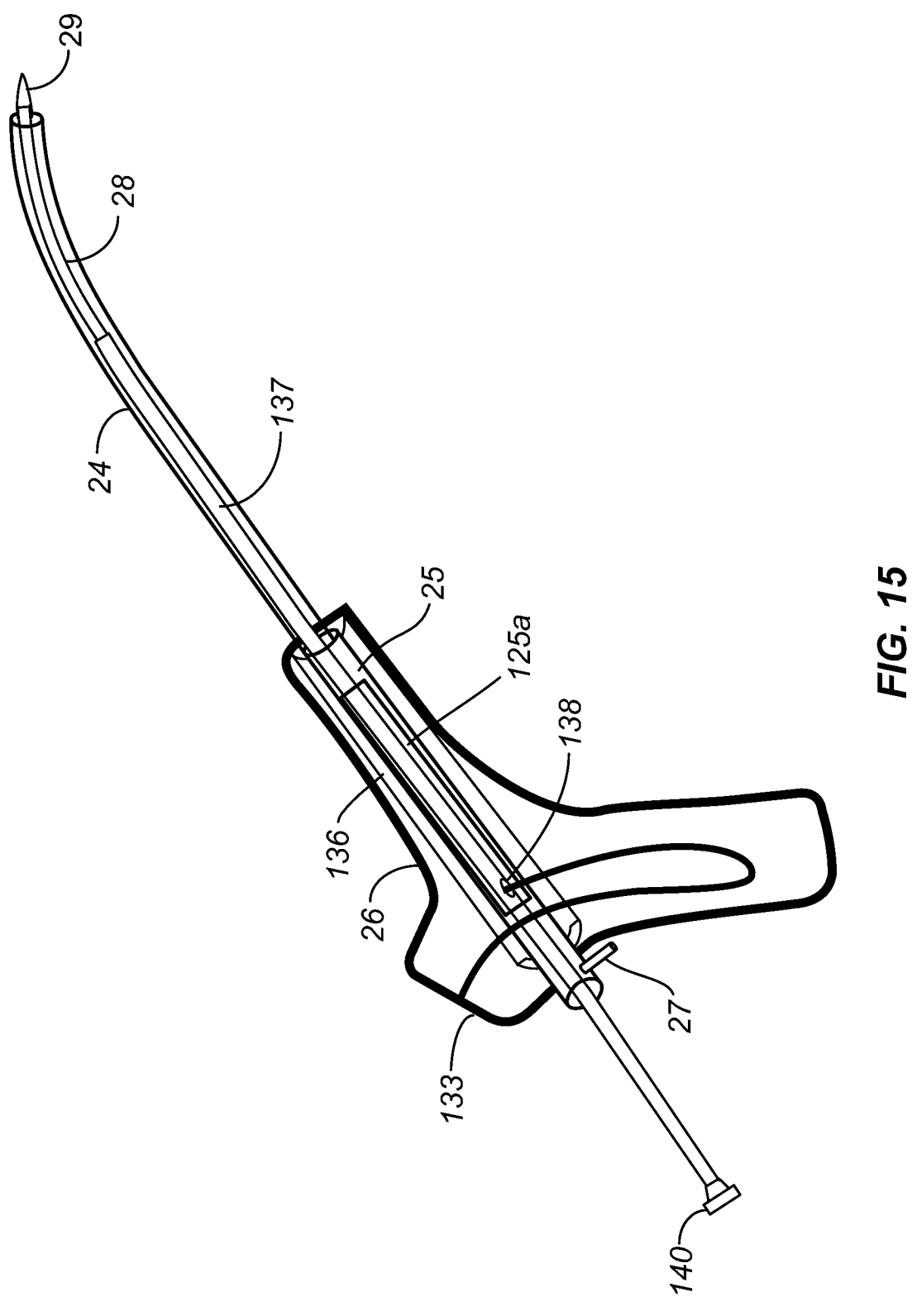
FIG. 15 shows the layout of the elements inside the handle of the manual oscillating endoscopic catheter for fallopian tube cannulation.

FIG. 15 is a view of the device with the handle 26 opened to reveal the configuration of the internal components. Cannula 24 is permanently attached to slotted tube 25.

Slotted tube 25 fits into recess 36 inside handle 26, such that it may rotate while being constrained against axial movement. Catheter 28 containing an attached transparent tapered tip 29, is sufficiently flexible to negotiate through the tortuous anatomy of the fallopian tube. A substantially rigid tube 137 is bonded to the proximal portion of transparent tapered tip catheter 28. While catheter 28 has an outer diameter of approximately 1 mm, rigid tube 137 has an outer diameter of approximately 3 mm. A polymer knob 140 attached to the proximal end of rigid tube 137 is grasped by the physician and used to advance the catheter 28 out of the cannula 24 with an oscillatory rotational motion.

Figure 16:
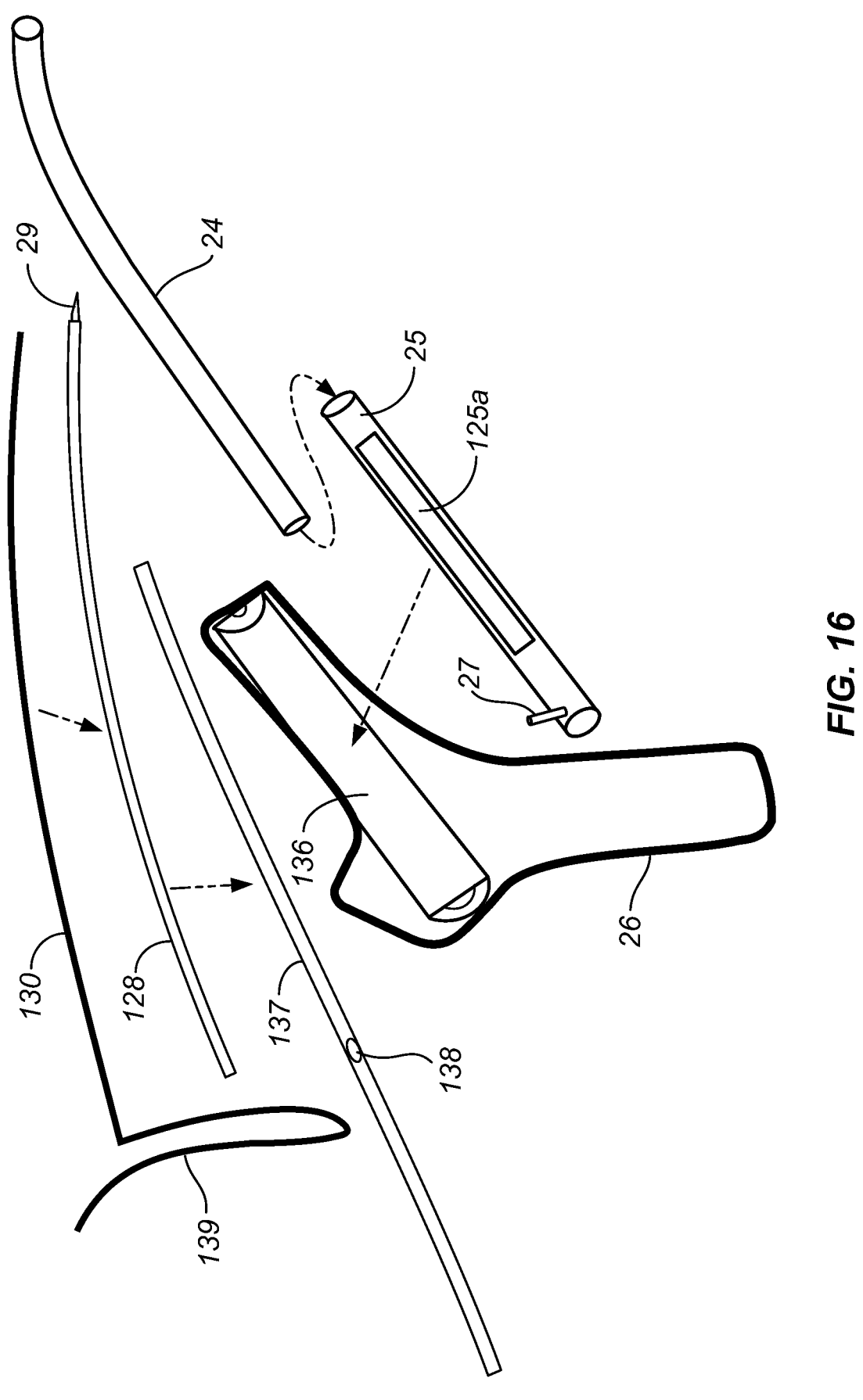
FIG. 16 depicts the exploded view of the elements inside the handle of the manual oscillating endoscopic catheter for fallopian tube cannulation.

FIG. 16 is an exploded view of the contents inside handle 26. A transparent tapered tip 29 is attached to the distal end of flexible catheter 28. A CMOS chip endoscope 130, comprised of a distal CMOS camera chip, flexible electronic cable and fiberoptic cables for light transmission, is bonded inside flexible catheter 28. A length of electronic and fiberoptic cables 139 extends out of the proximal end of catheter 28, for connection to the control circuit board and light emitting diodes. The proximal section of flexible catheter 28 is bonded to substantially rigid tube 137. The electronic and fiberoptic cables 139 exit opening 138 in rigid tube 137. Rigid tube 137 lies inside slotted tube 25, and the electronic and fiberoptic cables 139 exit slot 125 in slotted tube 25. Slot 125 has a length greater than 10 cm, to allow rigid tube 137 to advance a full 10 cm length distally, causing flexible catheter 28 to traverse the length of the fallopian tube. Slot 125 contains a width encompassing an arc of approximately 120°, allowing bi-directional rotation of rigid tube of approximately 60° in either direction. Slotted tube 25 drops into recess 136 in device handle 26. Rotational actuator 27 lies outside the proximal face of handle 26. Rotational actuator 27 may be a 3 mm diameter rod or pin attached to the proximal end of slotted tube 25, that is maneuvered to angle the tip of cannula 24 in line with the left or right os of the fallopian tube.

Figure 17:
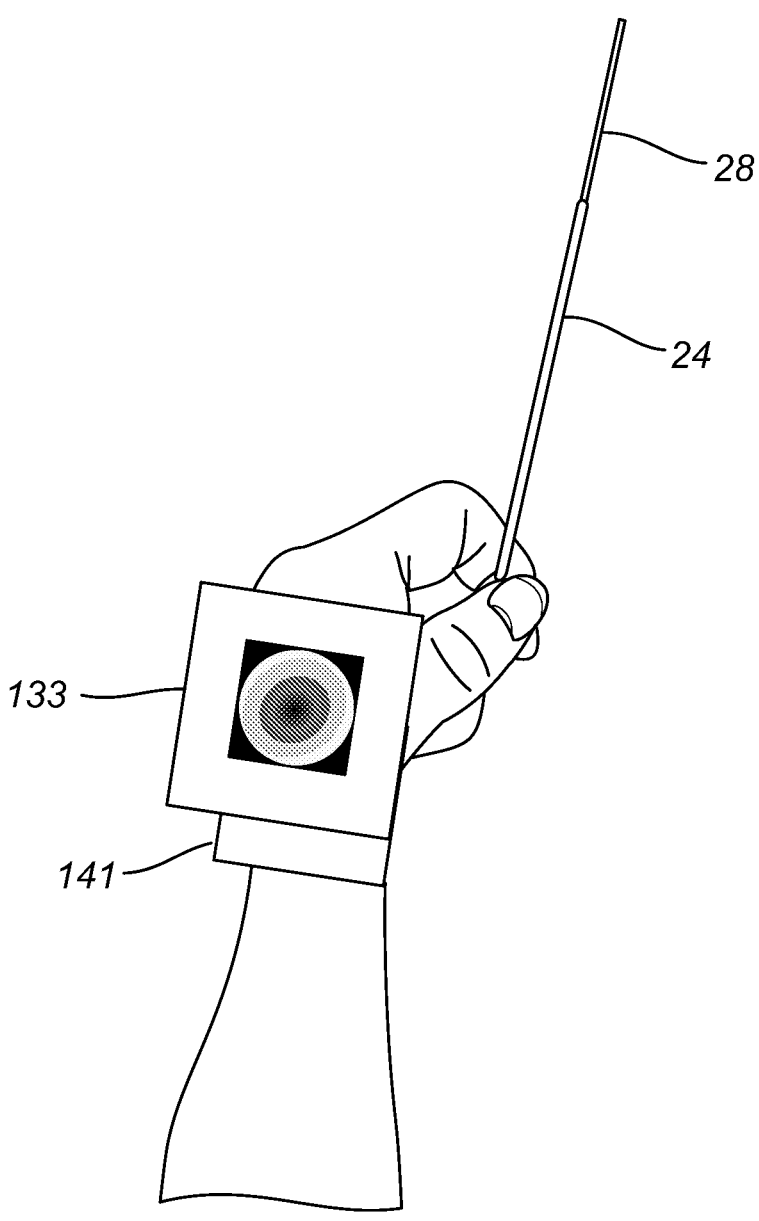
FIG. 17 shows an alternate positioning of the video monitor attached to a wristband on the operating physician.

FIG. 17 depicts an alternate embodiment of the device with the video monitor 133 attached to the physician's wrist via a wristband 141. The proximal portion of the cannula 24 is grasped by the operator, and the inner endoscopic catheter 28 is advanced through the fallopian tube with an oscillating motion. The cannula 24 exhibits a small profile compared with the previous handle, enhancing visualization of the patient's surface anatomy during operation of the device.

Figure 18:
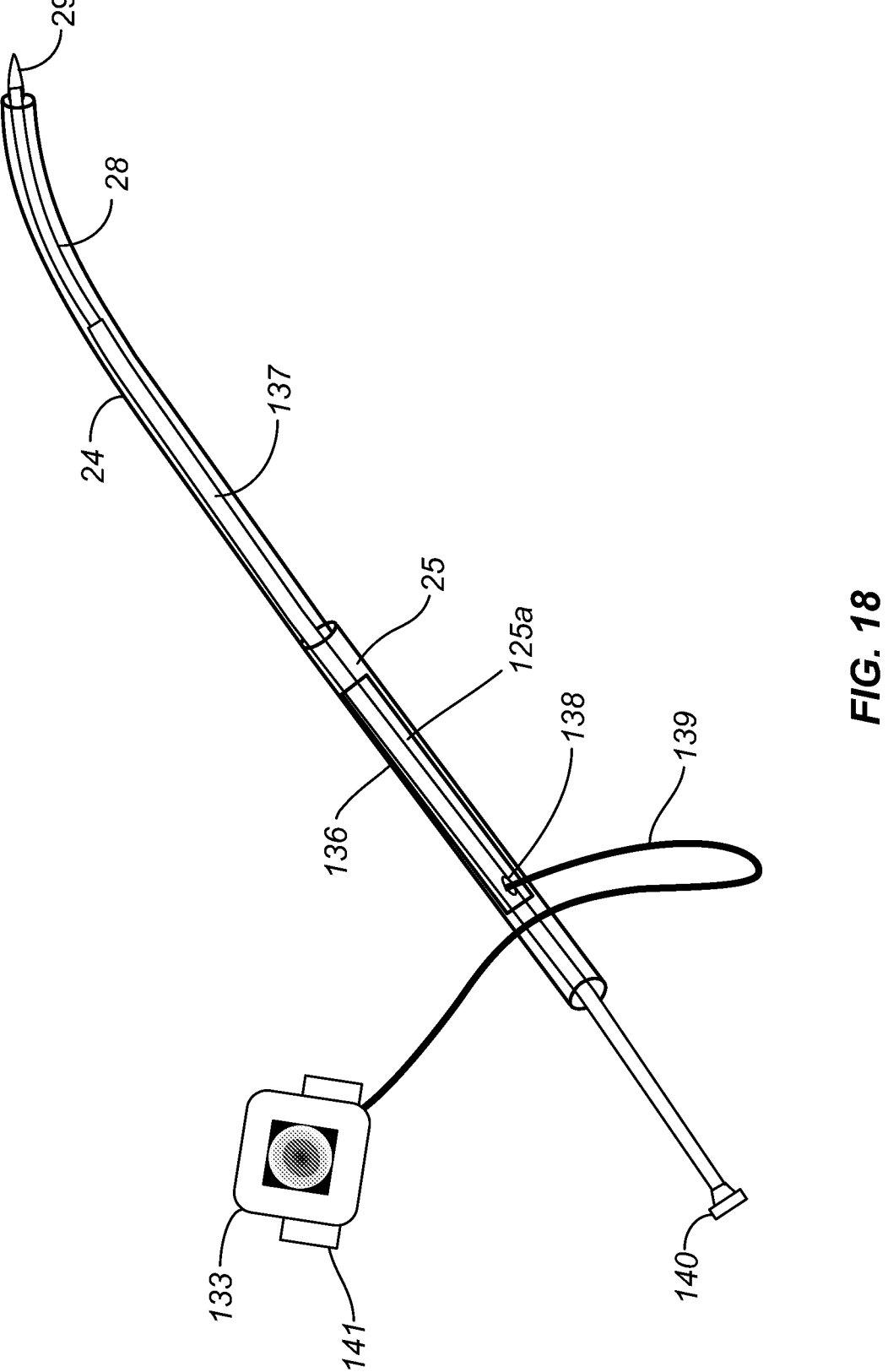
FIG. 18 depicts the components and configuration of the manual oscillating endoscopic catheter incorporating a wrist attachment of the video monitor instead of a device handle.

FIG. 18 shows the configuration of the device containing no handle. Cannula 24 is attached to slotted tube 25, and catheter 28 containing an attached transparent tapered tip 29, resides inside the cannula 24. A substantially rigid tube 137 is bonded to the proximal portion of transparent tapered tip catheter 28. A knob 140 on the proximal end of rigid tube 137 may be grasped by the physician and used to advance catheter 28 with an oscillating motion. Electronic and fiberoptic cables 139 are connected to the endoscope inside catheter 28 exit opening 138 in rigid tube 137 and slot 125 in slotted tube 25. Electronic and fiberoptic cables 39 connect to video monitor unit 133, containing a wrist band 141 that attaches to the wrist of the physician operating the device.

While the present invention has been described herein with respect to certain illustrated embodiments, those of ordinary skill in the art will recognize and appreciate that it is not so limited. Rather, many additions, deletions, and modifications to the illustrated embodiments may be made without departing from the scope of the invention as claimed, including legal equivalents thereof. In addition, features from one embodiment may be combined with features of another embodiment while still being encompassed within the scope of the invention as contemplated by the inventors. Further, embodiments of the disclosure have utility with different and various tool types and configurations.

What is claimed is:

1. A falloposcope comprising:
a cannula having an angled tip oriented to engage a fallopian os when the cannula is transcervically introduced to a patient's uterus;
a catheter having a distal viewing tip configured to be advanced from a distal end of the cannula into the patient's uterus through a cervical os;
a viewing chamber having a wide proximal end attached to the distal viewing tip of the catheter, wherein the viewing chamber is at least partially transparent and tapers in a distal direction to provide both a clear viewing zone for the endoscope and atraumatic advancement into the fallopian tube; and
a cell collection element located on an exterior of the catheter proximal of the viewing chamber.

2. The falloposcope of claim 1, wherein the viewing chamber is fully transparent.

3. The falloposcope of claim 1, wherein the viewing chamber comprises a pre-shaped, inflatable shell.

4. The falloposcope of claim 3, wherein the pre-shaped shell is conical in shape.

5. The falloposcope of claim 4, wherein the catheter has a diameter in a range from 0.75 mm to I mm, the base of the pre-shaped shell has a base diameter in a range from 1 mm to 1.25 mm and a length in a range from 4 mm to 7.5 mm when inflated.

6. The falloposcope of claim 1, further comprising a handle attached to a proximal end of the cannula and configured to distally advance the catheter from the distal end of the cannula.

7. The falloposcope of claim 6, wherein the handle comprises a drive assembly configured to simultaneously advance and rotationally oscillate the catheter.

8. The falloposcope of claim 7, wherein the drive assembly comprises a trigger coupled to a ratchet mechanism configured to incrementally advance the catheter.

9. The falloposcope of claim 8, wherein the drive assembly further comprises a motor-driven rocker arm that engages and rotationally oscillates the catheter or an extension of the catheter.

10. The falloposcope of claim 8, wherein the drive assembly further comprises a pin fixed in the handle, wherein the pin tracks in a serpentine groove formed in an exterior surface of the catheter or an extension of the catheter to cause the catheter to rotationally oscillate as the catheter is advanced by the trigger and ratchet.

11. A method for accessing a patient's fallopian tube, said method comprising:
transcervically introducing a distal end of a cannula into the patient's uterus to engage the patient's fallopian tube os;
advancing a catheter having a distal viewing tip from a distal end of the cannula into the patient's fallopian tube through the patient's fallopian tube os;
atraumatically advancing the catheter through the patient's fallopian tube while viewing an interior of the fallopian tube through a tapered viewing chamber attached to the distal viewing tip of the catheter, wherein astraumatically advancing the catheter comprises manually grasping a proximal end of the catheter; and collecting a cell from the fallopian tube, via a cell collection element, wherein the cell collection element is located on an exterior of the catheter proximal of the tapered viewing chamber.

12. The method of claim 11, wherein atraumatically advancing the catheter further comprises manually translating and/or rotating the catheter while sensing tactile feedback.

13. A falloposcope comprising:

a cannula having an angled tip oriented to engage a fallopian os when the cannula is transcervically introduced to a patient's uterus;

a catheter having a distal viewing tip configured to be advanced from a distal end of the cannula into the patient's uterus through a cervical os;

a viewing chamber having a wide proximal end attached to the distal viewing tip of the catheter; and a cell collection element located on an exterior of the catheter proximal of the viewing chamber, wherein the catheter is translatably and rotationally received in a lumen of the cannula and wherein a proximal end of the catheter is configured to be manually grasped by a user to allow manual translation and rotation with tactile feedback.

14. The falloposcope of claim 13, wherein the viewing chamber is at least partially transparent and tapers in a distal direction to provide both a clear viewing zone for the endoscope and atraumatic advancement into the fallopian tube.

\* \* \* \* \*